(12) United States Patent
Gowans et al.

(10) Patent No.: US 11,766,365 B2
(45) Date of Patent: *Sep. 26, 2023

(54) NEGATIVE PRESSURE WOUND THERAPY APPARATUS

(71) Applicant: Smith & Nephew PLC, Watford (GB)

(72) Inventors: John Philip Gowans, Hessle (GB); Bryan Greener, York (GB); Stephanie Jane Noble, Brough (GB)

(73) Assignee: Smith & Nephew PLC, Watford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/844,612

(22) Filed: Jun. 20, 2022

(65) Prior Publication Data
US 2022/0387225 A1     Dec. 8, 2022

Related U.S. Application Data

(63) Continuation of application No. 16/066,857, filed as application No. PCT/EP2016/082353 on Dec. 22, 2016, now Pat. No. 11,364,150.
(Continued)

(51) Int. Cl.
*A61F 13/02*     (2006.01)
*A61F 13/00*     (2006.01)
*A61M 1/00*     (2006.01)

(52) U.S. Cl.
CPC .... *A61F 13/0216* (2013.01); *A61F 13/00029* (2013.01); *A61F 13/00068* (2013.01);
(Continued)

(58) Field of Classification Search
CPC ............ A61F 13/0216; A61F 13/00029; A61F 13/00068
See application file for complete search history.

(56) References Cited

U.S. PATENT DOCUMENTS 3,972,328 A    8/1976   Chen
4,029,598 A    6/1977   Neisius et al.
(Continued)

FOREIGN PATENT DOCUMENTS

CA     2951043 A1    12/2015
DE     3443101 A1     5/1986
(Continued)

OTHER PUBLICATIONS

Advantec MFS, Inc., "Membrane Filters" (catalog), retrieved from http://www.advantecmfs.com/catalog/filt/membrane.pdf, on Jan. 29, 2016, Copyright 2001-2011, 17 pages.
(Continued)

*Primary Examiner* — Catharine L Anderson
*Assistant Examiner* — Arjuna P Chatrathi
(74) *Attorney, Agent, or Firm* — Knobbe, Martens Olson & Bear, LLP

(57) ABSTRACT

Disclosed embodiments relate to apparatuses and methods for wound treatment. In certain embodiments, a negative pressure wound therapy apparatus can include a spacer layer with an upper portion and a lower portion. The spacer layer can be configured to be wrapped around at least one edge of the absorbent layer with the upper portion of the spacer layer being above the absorbent layer and the lower portion of the spacer layer being below the absorbent layer. In some embodiments, a negative pressure wound therapy apparatus can include a first and second spacer layer and an absorbent layer. The first spacer layer can be positioned below the absorbent layer and the first spacer layer can have a perimeter larger than a perimeter of the absorbent layer. The second spacer layer can be positioned above the absorbent layer. The second spacer layer can have a perimeter larger than the perimeter of the absorbent layer.

13 Claims, 15 Drawing Sheets

Related U.S. Application Data

(60) Provisional application No. 62/273,038, filed on Dec. 30, 2015, provisional application No. 62/273,200, filed on Dec. 30, 2015.

(52) U.S. Cl.
CPC .............. *A61M 1/90* (2021.05); *A61M 1/915* (2021.05); *A61M 1/985* (2021.05); *A61F 13/00012* (2013.01); *A61F 13/00017* (2013.01); *A61F 13/0223* (2013.01); *A61F 2013/00153* (2013.01); *A61M 1/912* (2021.05); *A61M 1/913* (2021.05); *A61M 2205/75* (2013.01)

(56) References Cited

U.S. PATENT DOCUMENTS

| | | |
|---|---|---|
| 4,728,499 A | 3/1988 | Fehder |
| 4,813,942 A | 3/1989 | Alvarez |
| 5,056,510 A | 10/1991 | Gilman |
| 5,181,905 A | 1/1993 | Flam |
| 5,238,732 A | 8/1993 | Krishnan |
| 5,549,584 A | 8/1996 | Gross |
| 5,707,499 A | 1/1998 | Joshi et al. |
| 5,759,570 A | 6/1998 | Arnold |
| 5,852,126 A | 12/1998 | Barnard et al. |
| 6,071,267 A | 6/2000 | Zamierowski |
| 6,626,891 B2 | 9/2003 | Ohmstede |
| 6,685,681 B2 | 2/2004 | Lockwood et al. |
| 6,752,794 B2 | 6/2004 | Lockwood et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,070,584 B2 | 7/2006 | Johnson et al. |
| 7,108,683 B2 | 9/2006 | Zamierowski |
| 7,216,651 B2 | 5/2007 | Argenta et al. |
| 7,361,184 B2 | 4/2008 | Joshi |
| 7,381,859 B2 | 6/2008 | Hunt et al. |
| 7,569,742 B2 | 8/2009 | Haggstrom et al. |
| 7,605,298 B2 | 10/2009 | Bechert et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,718,249 B2 | 5/2010 | Russell et al. |
| 7,722,582 B2 | 5/2010 | Lina et al. |
| 7,749,531 B2 | 7/2010 | Booher |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| 8,007,257 B2 | 8/2011 | Heaton et al. |
| 8,034,037 B2 | 10/2011 | Adams et al. |
| 8,062,272 B2 | 11/2011 | Weston |
| 8,062,331 B2 | 11/2011 | Zamierowski |
| 8,080,702 B2 | 12/2011 | Blott et al. |
| 8,118,794 B2 | 2/2012 | Weston |
| 8,152,785 B2 | 4/2012 | Vitaris |
| 8,162,907 B2 | 4/2012 | Heagle |
| 8,207,392 B2 | 6/2012 | Haggstrom et al. |
| 8,235,972 B2 | 8/2012 | Adahan |
| 8,241,261 B2 | 8/2012 | Randolph et al. |
| 8,282,611 B2 | 10/2012 | Weston |
| 8,303,552 B2 | 11/2012 | Weston |
| 8,372,049 B2 | 2/2013 | Jaeb et al. |
| 8,372,050 B2 | 2/2013 | Jaeb et al. |
| 8,425,478 B2 | 4/2013 | Olson |
| 8,444,612 B2 | 5/2013 | Patel et al. |
| 8,460,255 B2 | 6/2013 | Joshi et al. |
| 8,513,481 B2 | 8/2013 | Gergely et al. |
| 8,535,283 B2 | 9/2013 | Heaton et al. |
| 8,540,688 B2 | 9/2013 | Eckstein et al. |
| 8,545,466 B2 | 10/2013 | Andresen et al. |
| 8,556,871 B2 | 10/2013 | Mormino et al. |
| 8,568,386 B2 | 10/2013 | Malhi |
| 8,628,505 B2 | 1/2014 | Weston |
| 8,641,691 B2 | 2/2014 | Fink et al. |
| 8,663,198 B2 | 3/2014 | Buan et al. |
| 8,679,079 B2 | 3/2014 | Heaton et al. |
| 8,715,256 B2 | 5/2014 | Greener |
| 8,764,732 B2 | 7/2014 | Hartwell |
| 8,795,243 B2 | 8/2014 | Weston |
| 8,795,800 B2 | 8/2014 | Evans |
| 8,808,274 B2 | 8/2014 | Hartwell |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,864,748 B2 | 10/2014 | Coulthard et al. |
| 8,956,335 B2 | 2/2015 | Zamierowski et al. |
| 8,956,336 B2 | 2/2015 | Haggstrom et al. |
| 9,012,714 B2 | 4/2015 | Fleischmann |
| 9,050,210 B2 | 6/2015 | Olson |
| 9,061,095 B2 | 6/2015 | Adie et al. |
| 9,067,003 B2 | 6/2015 | Buan et al. |
| 9,127,665 B2 | 9/2015 | Locke et al. |
| 9,168,330 B2 | 10/2015 | Joshi et al. |
| 9,199,012 B2 | 12/2015 | Vitaris et al. |
| 9,220,822 B2 | 12/2015 | Hartwell |
| 9,283,118 B2 | 3/2016 | Locke et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,421,309 B2 | 8/2016 | Robinson et al. |
| 9,427,505 B2 | 8/2016 | Askem et al. |
| 9,446,178 B2 | 9/2016 | Blott et al. |
| 9,452,248 B2 | 9/2016 | Blott et al. |
| 9,474,661 B2 | 10/2016 | Fouillet et al. |
| 9,629,986 B2 | 4/2017 | Patel et al. |
| 9,669,138 B2 | 6/2017 | Joshi et al. |
| 9,681,993 B2 | 6/2017 | Wu et al. |
| 9,795,725 B2 | 10/2017 | Joshi et al. |
| 9,808,561 B2 | 11/2017 | Adie et al. |
| 9,829,471 B2 | 11/2017 | Hammond et al. |
| 9,844,473 B2 | 12/2017 | Blott et al. |
| 9,956,121 B2 | 5/2018 | Hartwell |
| 9,962,474 B2 | 5/2018 | Greener |
| 11,364,150 B2 * | 6/2022 | Gowans .................. A61M 1/90 |
| 2001/0043943 A1 | 11/2001 | Coffey |
| 2003/0125646 A1 | 7/2003 | Whitlock |
| 2003/0208176 A1 | 11/2003 | Waksmundzki et al. |
| 2003/0208179 A1 | 11/2003 | Fuchs et al. |
| 2004/0057855 A1 | 3/2004 | Gerlach et al. |
| 2005/0143697 A1 | 6/2005 | Riesinger |
| 2006/0009744 A1 | 1/2006 | Erdman et al. |
| 2007/0040454 A1 | 2/2007 | Freudenberger et al. |
| 2007/0055209 A1 | 3/2007 | Patel et al. |
| 2007/0225663 A1 | 9/2007 | Watt et al. |
| 2007/0255194 A1 | 11/2007 | Gudnason et al. |
| 2008/0031748 A1 | 2/2008 | Ihle et al. |
| 2008/0132821 A1 | 6/2008 | Propp et al. |
| 2008/0200905 A1 | 8/2008 | Heaton et al. |
| 2008/0306456 A1 | 12/2008 | Riesinger |
| 2009/0125004 A1 | 5/2009 | Shen et al. |
| 2009/0157024 A1 | 6/2009 | Song |
| 2009/0227969 A1 | 9/2009 | Jaeb et al. |
| 2009/0234306 A1 | 9/2009 | Vitaris |
| 2009/0275922 A1 | 11/2009 | Coulthard et al. |
| 2009/0299251 A1 | 12/2009 | Buan |
| 2009/0299306 A1 | 12/2009 | Buan |
| 2010/0125258 A1 | 5/2010 | Coulthard et al. |
| 2010/0259406 A1 | 10/2010 | Caso et al. |

(56) References Cited

U.S. PATENT DOCUMENTS

| | | |
|---|---|---|
| 2010/0305490 A1 | 12/2010 | Coulthard et al. |
| 2010/0318052 A1 | 12/2010 | Ha et al. |
| 2010/0324510 A1 | 12/2010 | Andresen et al. |
| 2011/0004168 A1 | 1/2011 | Eriksson et al. |
| 2011/0004172 A1 | 1/2011 | Eckstein et al. |
| 2011/0028918 A1 | 2/2011 | Hartwell |
| 2011/0060204 A1 | 3/2011 | Weston |
| 2011/0118683 A1 | 5/2011 | Weston |
| 2011/0224631 A1 | 9/2011 | Simmons et al. |
| 2011/0295220 A1 | 12/2011 | Heaton et al. |
| 2012/0051945 A1 | 3/2012 | Orndorff et al. |
| 2013/0066285 A1 | 3/2013 | Locke et al. |
| 2013/0066289 A1 | 3/2013 | Song et al. |
| 2013/0090615 A1 | 4/2013 | Jaeb et al. |
| 2013/0090616 A1 | 4/2013 | Neubauer |
| 2013/0102979 A1 | 4/2013 | Coulthard et al. |
| 2013/0123728 A1 | 5/2013 | Pratt et al. |
| 2013/0138054 A1 | 5/2013 | Fleischmann |
| 2013/0144227 A1 | 6/2013 | Locke et al. |
| 2013/0150814 A1 | 6/2013 | Buan |
| 2013/0165878 A1 | 6/2013 | Heagle |
| 2013/0274688 A1 | 10/2013 | Weston |
| 2013/0296762 A1 | 11/2013 | Toth |
| 2013/0302545 A1 | 11/2013 | Schnelker et al. |
| 2013/0338614 A1 | 12/2013 | Heaton et al. |
| 2014/0039423 A1 | 2/2014 | Riesinger |
| 2014/0100539 A1 | 4/2014 | Coulthard et al. |
| 2014/0114268 A1 | 4/2014 | Auguste et al. |
| 2014/0127148 A1 | 5/2014 | Derain |
| 2014/0155849 A1 | 6/2014 | Heaton et al. |
| 2014/0188061 A1 | 7/2014 | Locke et al. |
| 2014/0188090 A1 | 7/2014 | Riesinger |
| 2014/0200533 A1 | 7/2014 | Whyte et al. |
| 2014/0200535 A1 | 7/2014 | Locke et al. |
| 2014/0249495 A1 | 9/2014 | Mumby et al. |
| 2014/0276490 A1 | 9/2014 | Locke et al. |
| 2014/0276491 A1 | 9/2014 | Luckemeyer et al. |
| 2014/0276497 A1 | 9/2014 | Robinson et al. |
| 2014/0277454 A1 | 9/2014 | Locke et al. |
| 2014/0303575 A1 | 10/2014 | May |
| 2014/0309601 A1 | 10/2014 | Hall et al. |
| 2014/0316359 A1 | 10/2014 | Collinson et al. |
| 2014/0350496 A1 | 11/2014 | Riesinger |
| 2015/0032035 A1 | 1/2015 | Banwell et al. |
| 2015/0065965 A1 | 3/2015 | Haggstrom et al. |
| 2015/0119831 A1 | 4/2015 | Robinson et al. |
| 2015/0119832 A1 | 4/2015 | Locke |
| 2015/0119833 A1 | 4/2015 | Coulthard et al. |
| 2015/0141941 A1 | 5/2015 | Allen et al. |
| 2016/0000611 A1 | 1/2016 | Riesinger |
| 2016/0000611 A1 | 1/2016 | Niederauer et al. |
| 2016/0081859 A1 | 3/2016 | Hartwell |
| 2016/0136339 A1 | 5/2016 | Begin et al. |
| 2016/0144084 A1 | 5/2016 | Collinson et al. |
| 2016/0262942 A1 | 9/2016 | Riesinger |
| 2016/0298620 A1 | 10/2016 | Cordoba et al. |
| 2016/0317357 A1 | 11/2016 | Vitaris et al. |
| 2017/0128642 A1 | 5/2017 | Buan |
| 2017/0181896 A1 | 6/2017 | Hartwell |
| 2017/0181897 A1 | 6/2017 | Hartwell |
| 2017/0368239 A1 | 12/2017 | Askem et al. |
| 2018/0133378 A1 | 5/2018 | Askem et al. |
| 2018/0318476 A1 | 11/2018 | Askem et al. |
| 2020/0121833 A9 | 4/2020 | Askem et al. |

FOREIGN PATENT DOCUMENTS

| | | |
|---|---|---|
| DE | 202004017052 U1 | 6/2005 |
| EP | 0340018 A2 | 11/1989 |
| EP | 1476217 B1 | 3/2008 |
| EP | 1955887 A2 | 8/2008 |
| EP | 2335749 A1 | 6/2011 |
| EP | 2462908 A1 | 6/2012 |
| EP | 2711034 A1 | 3/2014 |
| EP | 2305325 B1 | 4/2014 |
| EP | 2345437 B1 | 4/2014 |
| EP | 2563308 B1 | 3/2015 |
| EP | 2687245 B1 | 2/2016 |
| FR | 1163907 A | 10/1958 |
| GB | 1255395 A | 12/1971 |
| GB | 2307180 B | 6/2000 |
| GB | 2468905 A | 9/2010 |
| WO | WO-8300742 A1 | 3/1983 |
| WO | WO-9216245 A1 | 10/1992 |
| WO | WO-9605873 A1 | 2/1996 |
| WO | WO-2004077387 A1 | 9/2004 |
| WO | WO-2005025447 A2 | 3/2005 |
| WO | WO-2005046760 A1 | 5/2005 |
| WO | WO-2005105180 A1 | 11/2005 |
| WO | WO-2005123170 A1 | 12/2005 |
| WO | WO-2007113597 A2 | 10/2007 |
| WO | WO-2008039223 A1 | 4/2008 |
| WO | WO-2009066105 A1 | 5/2009 |
| WO | WO-2009124100 A1 | 10/2009 |
| WO | WO-2009147402 A2 | 12/2009 |
| WO | WO-2009158128 A2 | 12/2009 |
| WO | WO-2010142959 A2 | 12/2010 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012143665 A1 | 10/2012 |
| WO | WO-2013010907 A1 | 1/2013 |
| WO | WO-2013064852 A1 | 5/2013 |
| WO | WO-2013090810 A1 | 6/2013 |
| WO | WO-2013136181 A2 | 9/2013 |
| WO | WO-2013149078 A1 | 10/2013 |
| WO | WO-2014008348 A2 | 1/2014 |
| WO | WO-2014020440 A1 | 2/2014 |
| WO | WO-2014020443 A2 | 2/2014 |
| WO | WO-2014113253 A1 | 7/2014 |
| WO | WO-2015022340 A1 | 2/2015 |
| WO | WO-2015031216 A1 | 3/2015 |
| WO | WO-2015188003 A1 | 12/2015 |
| WO | WO-2016018448 A1 | 2/2016 |
| WO | WO-2016174048 A1 | 11/2016 |
| WO | WO-2017114745 A1 | 7/2017 |

OTHER PUBLICATIONS

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

International Preliminary Report on Patentability for Application No. PCT/EP2016/082353, dated Jul. 12, 2018, 11 pages.

International Search Report and Written Opinion for Application No. PCT/EP2016/082353, dated Mar. 8, 2017, 14 pages.

Kendall ULTEC Hydrocolloid Dressing (4×4"), Product Ordering Page, web page downloaded on Jul. 13, 2014, 1 page.

Protz K., "Modern Wound Dressings Support the Healing Process," Wound care: Indications and Application, Geriatrie Journal, Apr. 2005, pp. 3333-3339 (17 pages with English translation).

Smith & Nephew, "PICO Single Use Negative Pressure Wound Therapy System," Spiral Booklet, Mar. 2011, 7 pages.

Technology Watch, May 1989, 1 page.

* cited by examiner

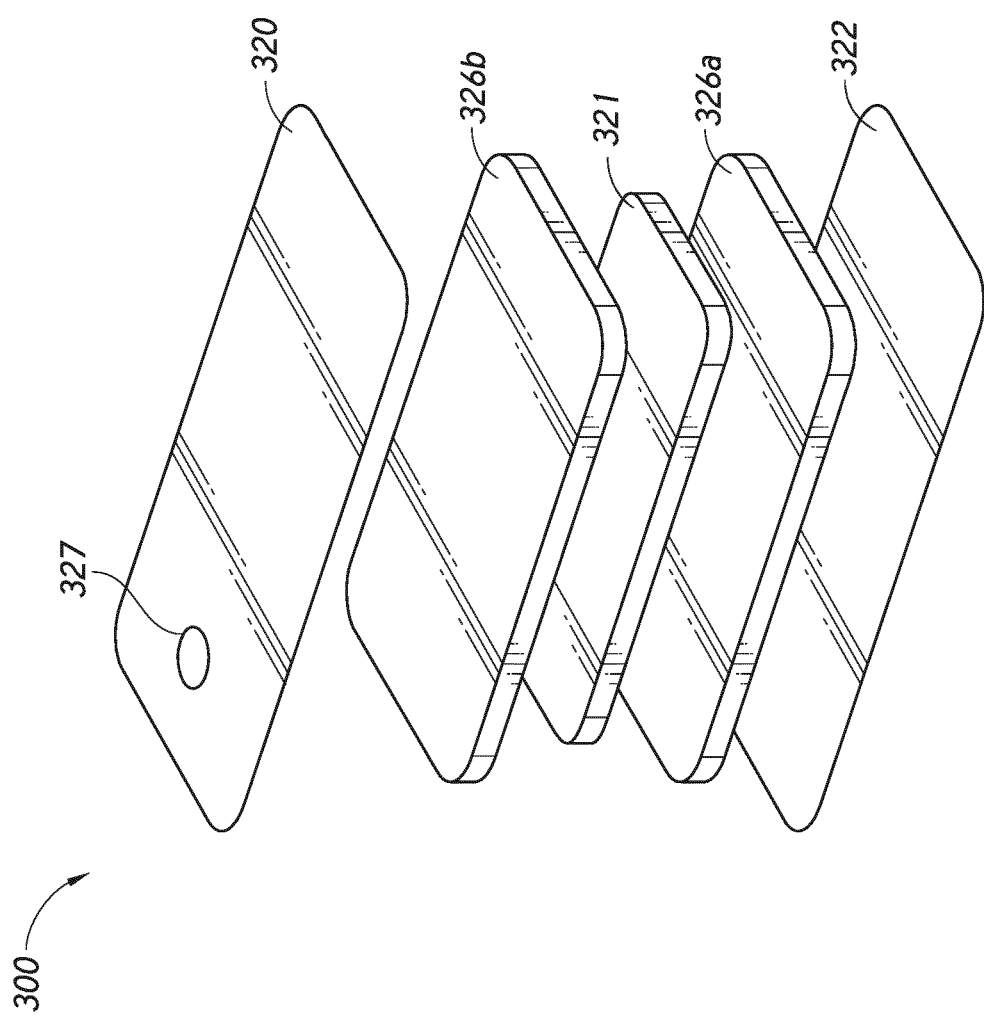

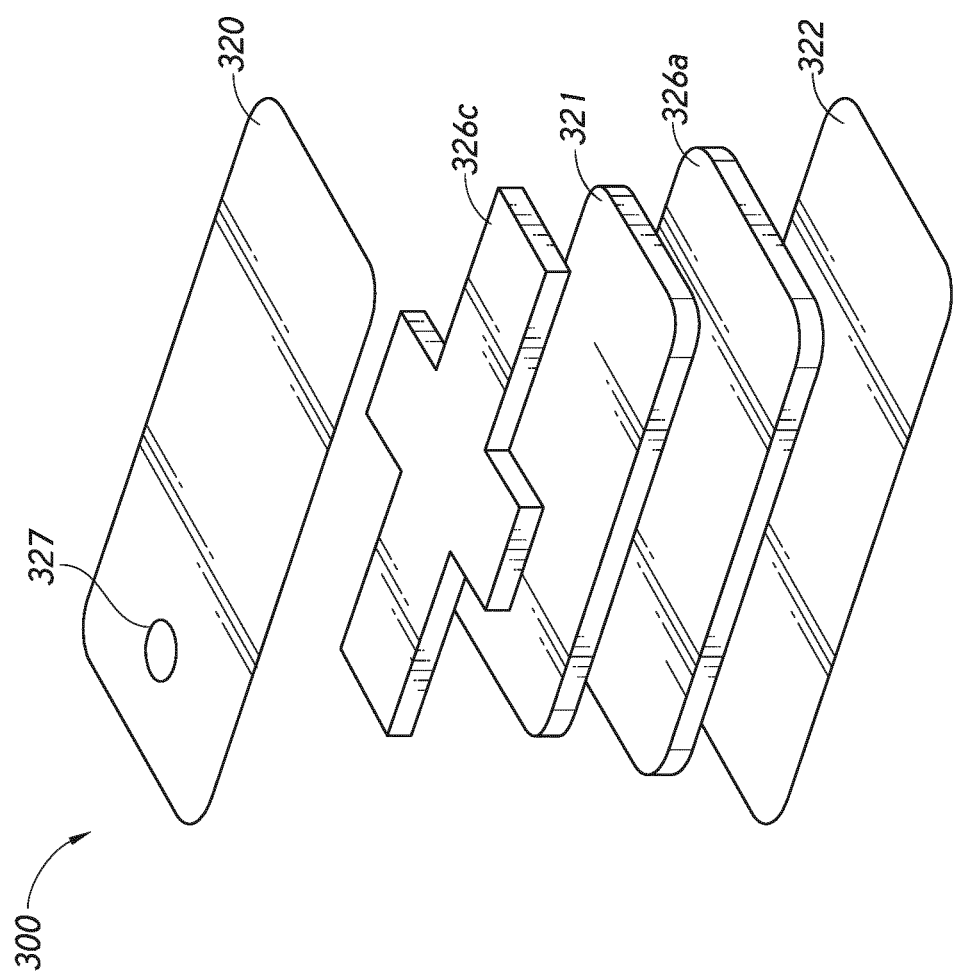

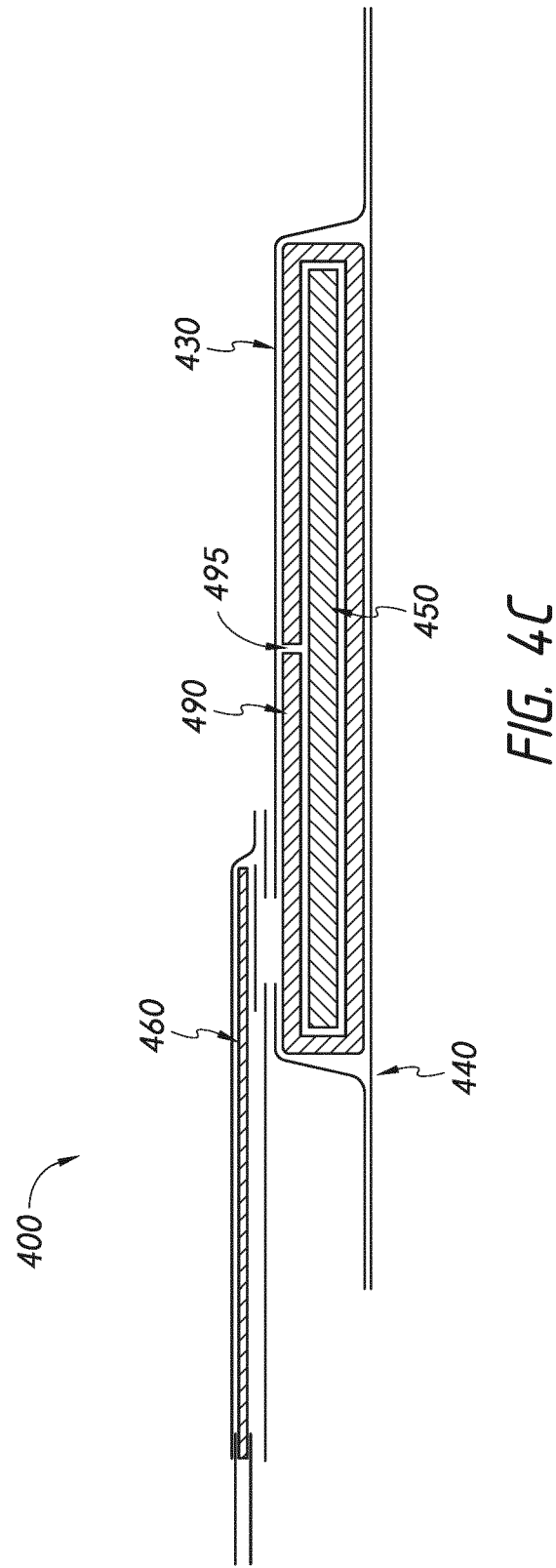

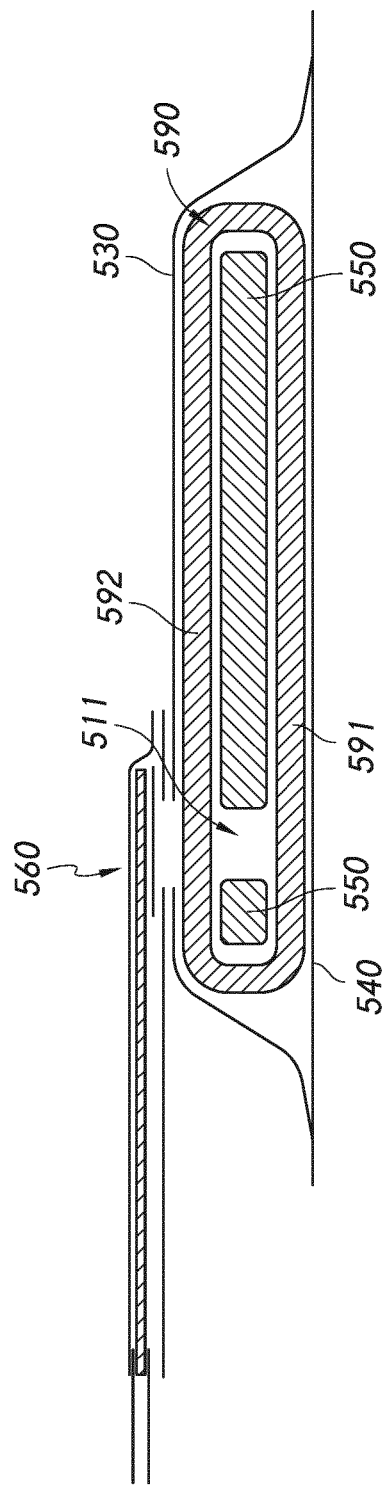

NEGATIVE PRESSURE WOUND THERAPY APPARATUS

CROSS-REFERENCE TO RELATED APPLICATIONS

This application is a continuation of U.S. application Ser. No. 16/066,857, filed Jun. 28, 2018, which is a U.S. national stage application of International Patent Application No. PCT/EP2016/082353, filed on Dec. 22, 2016, which claims the benefit of U.S. Provisional Application No. 62/273,038, filed Dec. 30, 2015, and U.S. Provisional Application No. 62/273,200, filed Dec. 30, 2015.

BACKGROUND

Technical Field

Embodiments described herein relate to apparatuses, systems, and methods the treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Wound dressings for use in negative pressure can have a lifetime of the wound dressing associated with the liquid absorbency capacity of the dressing. The shortened lifetime can be observed due to problems of the fluid pathway to the port being blocked before the dressing is at full absorbent capacity. It may be desirable, in some situations, to provide a fluid flow pathway that prevents or decreases the blocking of the port until the full lifetime of the dressing is achieved.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein.

In some aspects, a negative pressure wound therapy apparatus comprises a wound dressing. The wound dressing comprises a wound contact layer configured to be positioned in contact with a wound, a spacer layer, wherein the spacer layer comprises an upper portion and a lower portion and wherein the upper portion and lower portion of the spacer layer are configured to be in fluid communication, an absorbent layer, wherein the spacer layer is configured to be wrapped around at least one edge of the absorbent layer with the upper portion of the spacer layer being above the absorbent layer and the lower portion of the spacer layer being below the absorbent layer; and a cover layer configured to cover and form a seal over the wound contact layer, the spacer layer, and the absorbent layer.

The apparatus of the preceding paragraph may also include any combination of the following features described in this paragraph, among others described herein. The apparatus can include a negative pressure source configured to apply negative pressure through an opening in the cover layer. The apparatus can include a port provided over an opening in the cover layer, wherein the port comprises a filter. The apparatus can include a through-hole extending through the absorbent layer. The through-hole is aligned underneath the filter. The through-hole is offset from the filter. The upper portion of the spacer layer forms a cross-shape above the absorbent layer.

In some aspects, a negative pressure wound therapy apparatus comprises a wound dressing that comprises a wound contact layer configured to be positioned in contact with a wound, an absorbent layer, a first spacer layer below the absorbent layer, the first spacer layer having a perimeter larger than a perimeter of the absorbent layer, a second spacer layer above the absorbent layer, the second spacer layer having a perimeter larger than the perimeter of the absorbent layer, and a cover layer configured to cover and form a seal over the wound contact layer, the spacer layers, and the absorbent layer, the cover layer comprising an aperture, wherein the second spacer layer underlies the aperture in the cover layer, and a fluidic connector positioned over the opening in the cover layer; and a filter provided at the opening in the cover layer.

The apparatus of the preceding paragraph may also include any combination of the following features described in this paragraph, among others described herein. The apparatus can include a negative pressure source configured to apply negative pressure through the opening in the cover layer. The apparatus can include a plurality of absorbent layers between the first and second spacer layers. The second spacer layer forms a cross-shape above the absorbent layer.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIG. 3A illustrates an embodiment of a negative pressure wound treatment system employing a wound dressing capable of absorbing and storing wound exudate;

FIG. 3D illustrates an embodiment of a negative pressure wound treatment system employing a wound dressing capable of absorbing and storing wound exudate;

FIG. 4C illustrates a cross sectional view of an embodiment of a negative pressure wound treatment system employing a flexible fluidic connector and a wound dressing with a wrapped around spacer layer, the wound dressing capable of absorbing and storing wound exudate;

FIG. 4D illustrates a cross-section of an integrated wound dressing showing various layers according to another embodiment;

DETAILED DESCRIPTION

Figure 1A:
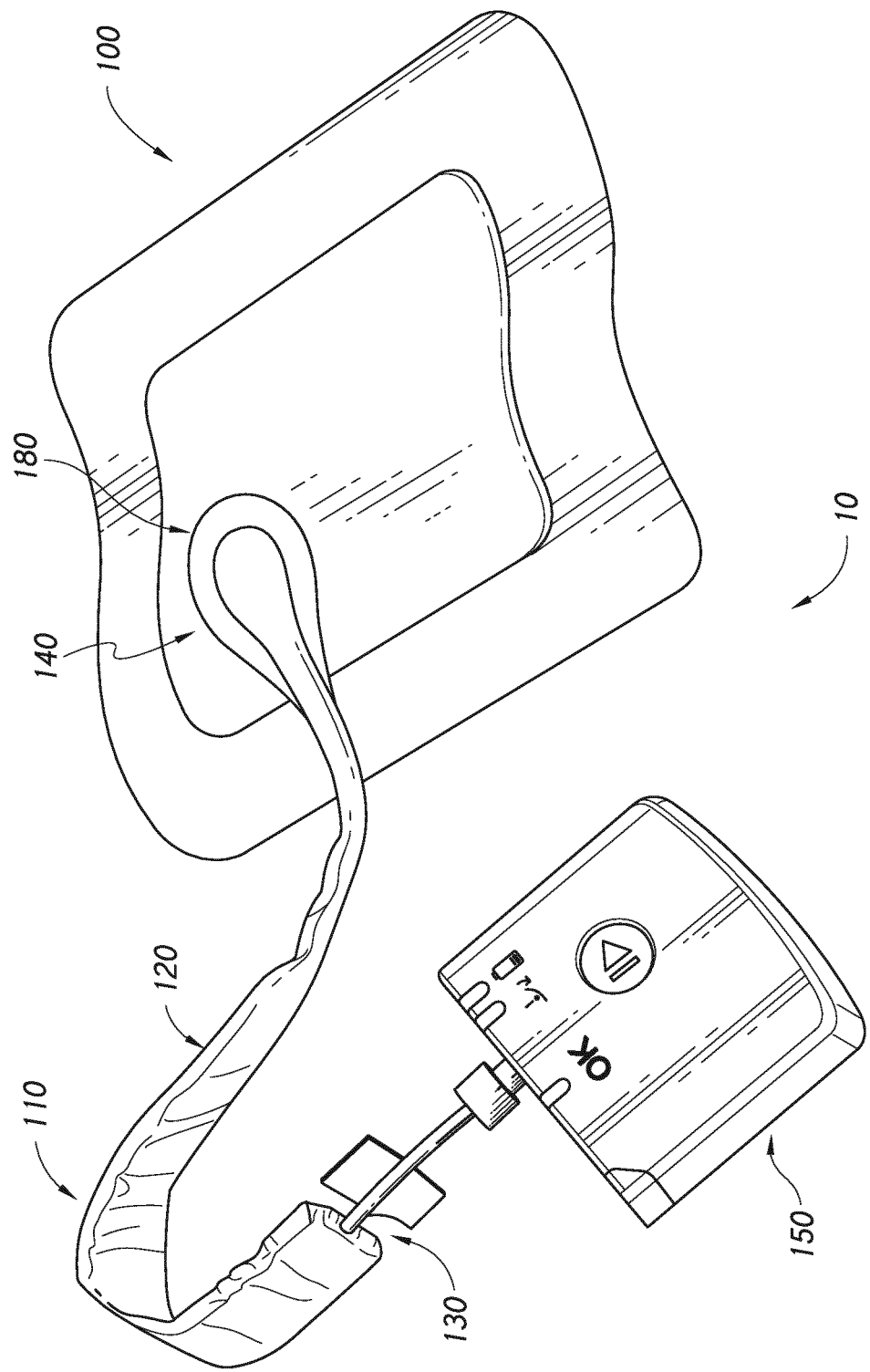
FIG. 1A illustrates an embodiment of a negative pressure wound treatment system employing a flexible fluidic connector and a wound dressing capable of absorbing and storing wound exudate.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., $-40$ mmHg is less than $-60$ mmHg). Negative pressure that is "more" or "greater" than $-X$ mmHg corresponds to pressure that is further from atmospheric pressure (e.g., $-80$ mmHg is more than $-60$ mmHg). In some embodiments, local ambient atmospheric pressure is used as a reference point, and such local atmospheric pressure may not necessarily be, for example, 760 mmHg.

The negative pressure range for some embodiments of the present disclosure can be approximately $-80$ mmHg, or between about $-20$ mmHg and $-200$ mmHg. Note that these pressures are relative to normal ambient atmospheric pressure, which can be 760 mmHg. Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,874, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158, titled "FLUIDIC CONNECTOR FOR NEGATIVE PRESSURE WOUND THERAPY," the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump and/or associated electronics described herein may also be used in combination or in addition to those described in International Application No. PCT/EP2016/059329, filed Apr. 26, 2016, published as WO2016174048 A1 on Nov. 3, 2016, titled "REDUCED PRESSURE APPARATUS AND METHODS."

Figure 1B:
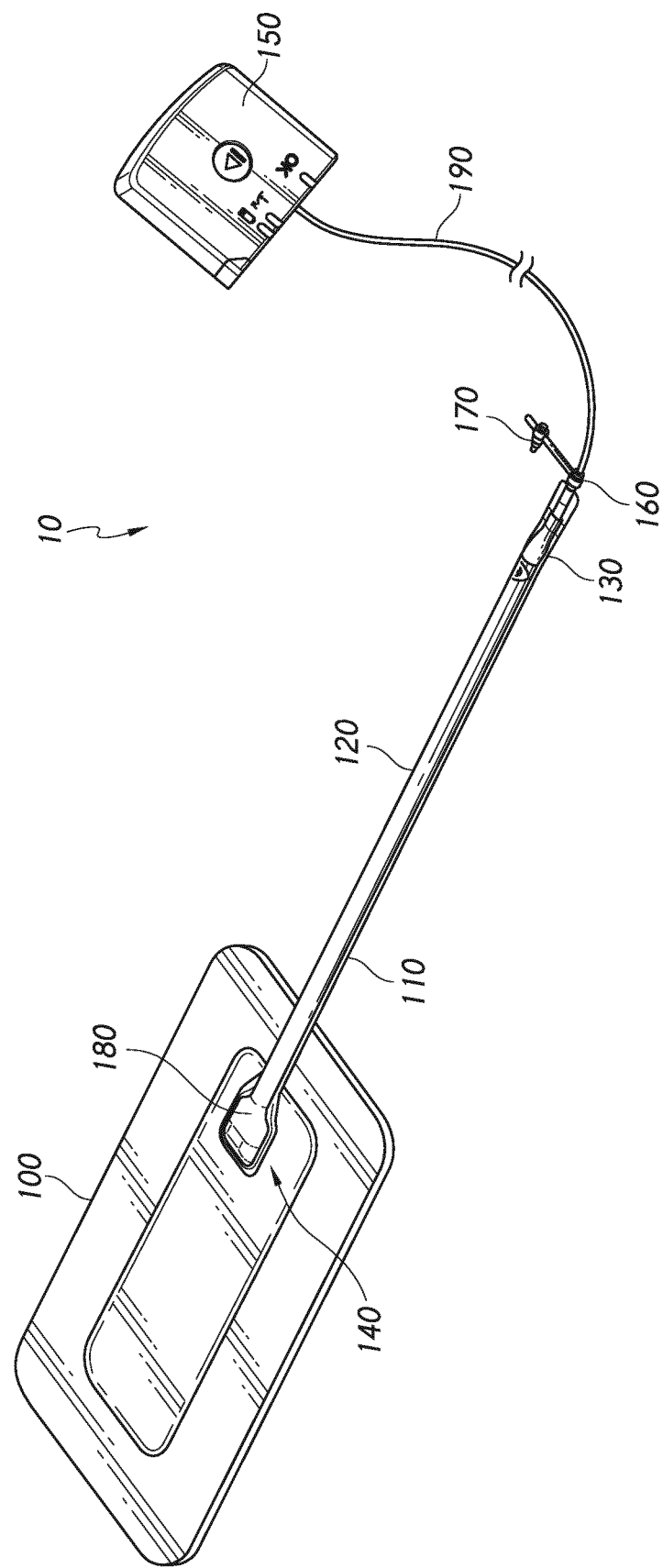
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved. In some embodiments, the pump can be miniaturized and portable, although larger conventional pumps may also be used with the dressing 100. In some embodiments, the pump may be attached or mounted onto or adjacent the dressing 100.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include a cover layer for positioning over the layers of the wound dressing. The cover layer can be the upper most layer of the dressing. In some embodiments, the wound dressing can include a second cover layer for positioning over the layers of the wound dressing and any of the integrated components. The second cover layer can be the upper most layer of the dressing or can be a separate envelope that encloses the integrated components of the topical negative pressure system.

Figure 2A:
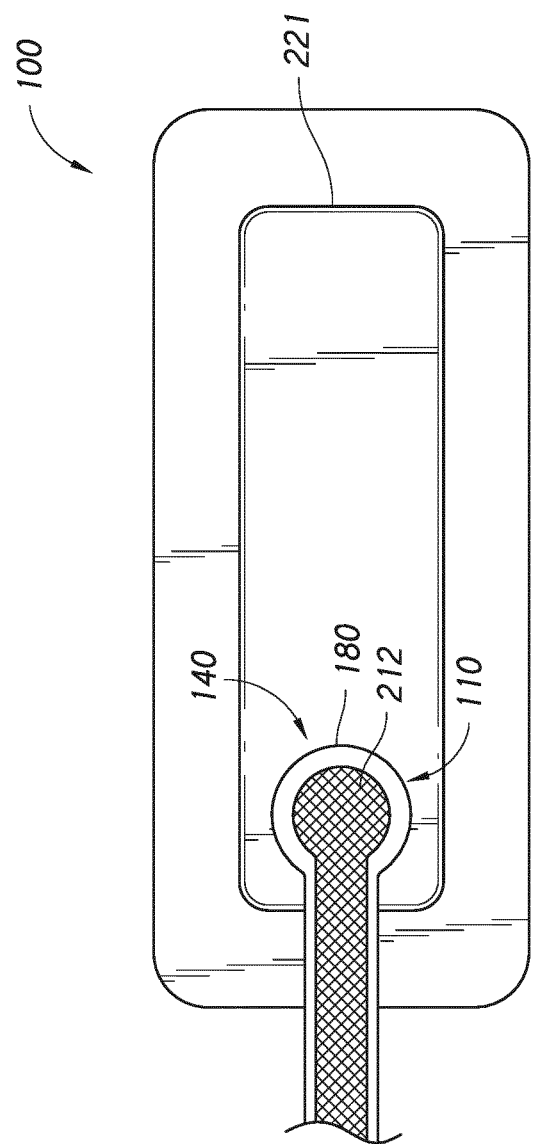
FIG. 2A illustrates an embodiment of a negative pressure wound treatment system employing a flexible fluidic connector and a wound dressing capable of absorbing and storing wound exudate.

As shown in FIG. 2A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 100 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 2B:
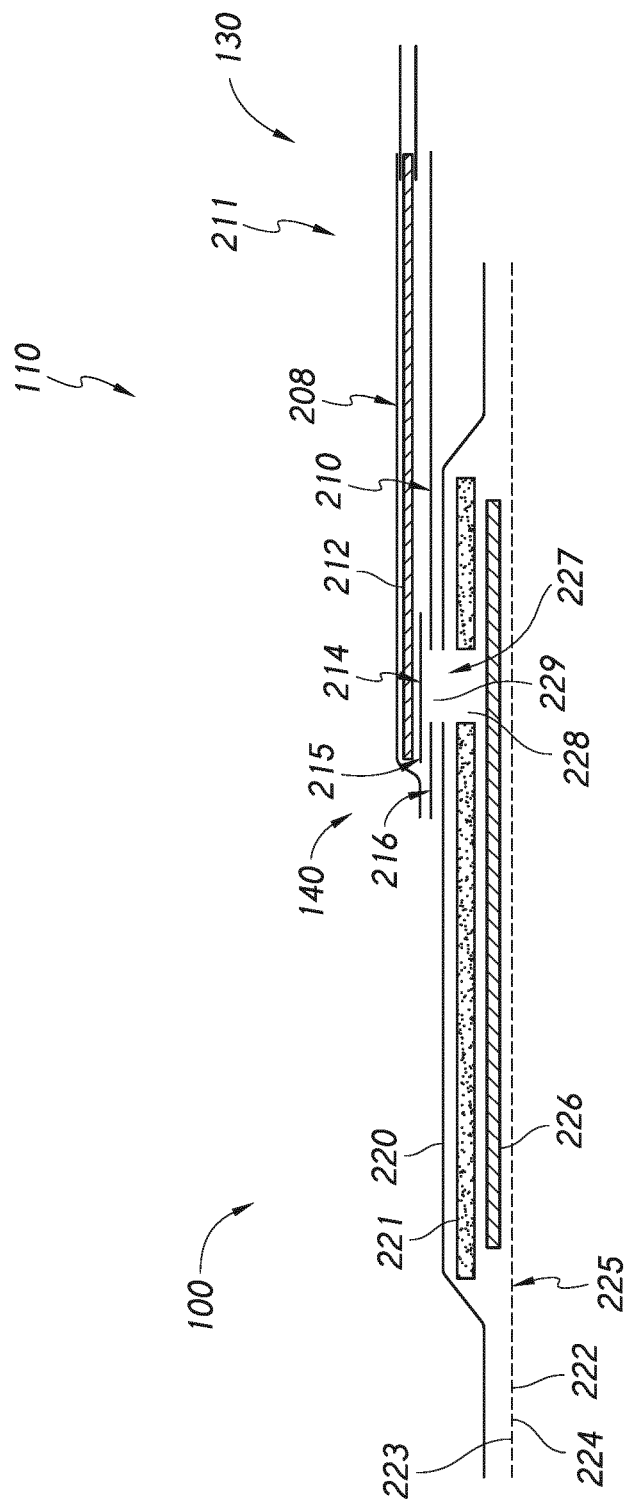
FIG. 2B illustrates a cross section of an embodiment of a fluidic connector connected to a wound dressing.

FIG. 2B illustrates a cross-section through a wound dressing 100 similar to the wound dressing 100 as shown in FIG. 1B and described in International Patent Publication WO2013175306 A2, filed May 22, 2013, entitled "APPARATUSES AND METHODS FOR NEGATIVE PRESSURE WOUND THERAPY", the disclosure of which is hereby incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™11C-450. In some embodiments, the absorbent layer 221 may comprise a composite comprising superabsorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 2B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in US Patent Publication 2015/0190286 A1, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which could seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 110, or the orifice 227.

In particular for embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 (described below) may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected to the sealing surface 216. The filter 214 is configured to substantially prevent wound exudate from entering the bridge.

Some embodiments may further comprise an optional second fluid passage positioned above the first fluid passage 212. For example, some embodiments may provide for an air leak may be disposed at the proximal end of the top layer 208 that is configured to provide an air path into the first fluid passage 212 and dressing 100 similar to the suction adapter as described in U.S. Pat. No. 8,801,685, filed Dec. 30, 2011, entitled "APPARATUSES AND METHODS FOR NEGATIVE PRESSURE WOUND THERAPY" the disclosure of which is hereby incorporated by reference in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid barrier and to ensure that no liquids are able to escape from the wound dressing 100. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Some wound dressings such as those described above can have a lifetime of just over 3 days when tested on a standard in vitro wound model. During these tests the dressing is considered to be functioning successfully if it maintains the target vacuum level (e.g., −80 mmHg) and mobile liquid is not visible within the dressing during testing or, at the time of vacuum failure, upon removal. The failure mode can be caused by a blocking of the semi-permeable membrane of the fluidic connector by the input liquid.

The wound model lifetime of an embodiment of the wound dressing can be determined by three major factors: (1) MVTR through the top film; (2) liquid absorbency capacity and (3) internal geometry. Regarding internal geometry, it is desirable that the dressing offers no means for the wet absorbent layer to block the fluid pathway to the fluidic connector prior to the dressing becoming full to its liquid capacity. Some embodiments of dressings fail at 3 days. This failure can be due to a combination of (2) and (3).

To extend the lifetime of the wound dressing features of the dressing can be altered to prevent the failure caused by protein-blocking of the filter of the fluidic connector. The dressing could be protein-blocked within its cross-section prior to the fluid reaching the fluidic connector by a semi-solid or solid crust of protein. The protein-blocking can be defined by three variables: the protein concentration of the input liquid, the moisture transmission rate through the backing layer, and the protein-absorbing ability of the absorbent layer. In some embodiments, superabsorbent particles comprising the absorbent layer can absorb water from the input liquid and concentrate the protein within the device. Also, in some embodiments, the protein crust could only block the dressing or filter membrane if it could form a continuous barrier to the vacuum supply. In the above dressings, this could occur relatively easily because the absorbent layer, positioned directly against the backing layer, provides a ready means of achieving blockage when it becomes saturated with liquid. To address this issue, some embodiments of the dressing can include the layered configuration as illustrated in FIG. 3A.

As shown in FIG. 3A, the wound dressing 300 can include a wound contact layer 322. The wound contact layer can be similar to the wound contact layer 322 described with reference to FIG. 2B. In some embodiments, the wound contact layer 322 can be a double-face coated (silicone-acrylic) perforated adhesive wound contact layer. A transmission layer 326a and absorbent layer 321 can be provided similar to the dressing described with reference to FIG. 2B but the transmission layer 326a over-borders the absorbent layer. The wound dressing 300 can include a second transmission layer 326b between the absorbent layer and the backing layer that over-borders the absorbent layer. The first and second transmission layers 326a and 326b can over-border the absorbent layer by 5 mm at the perimeter. This can be the reverse of the cut geometry in the dressings as described previously. In some embodiments, there is no through-hole or aperture in the absorbent layer 321 or second transmission layer 326b. In some embodiments, the hole in the absorbent layer could be disadvantageous because it could become filled with superabsorbent particles or other material and block the filter in the standard dressing. A backing layer 320 sits over the second transmission layer 326b and the backing layer can include an orifice 327 that allows connection of the fluidic connector to communicate negative pressure to the dressing.

In some embodiments, the first and second transmission layer 326a, 326b can include a 3D fabric as described herein. The first and second transmission layers 326a, 326b can allow transmission of fluid including liquid and gas away from a wound site into the layers of the wound dressing. In particular, the first and second transmission layers 326a, 326b preferably ensures that an open air channel can be maintained to communicate negative pressure over the wound area and throughout the wound dressing even when the absorbent layer has absorbed substantial amounts of exudates. The first and second transmission layers 326a, 326b may be formed of a material having a three dimensional structure. For example, a knitted or woven spacer fabric (for example Baltex 7970 weft knitted polyester) or a non-woven fabric could be used as described previously.

In some embodiments, the first transmission layer 326a comprises a 3D polyester spacer fabric layer including a top layer (that is to say, a layer distal from the wound-bed and in contact with the wound facing side of the absorbent layer in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

In some embodiments, the second transmission layer 326b comprises a 3D polyester spacer fabric layer including a bottom layer (that is to say, a layer proximal to the wound-bed and in contact with the top side of the absorbent layer in use) which is a 84/144 textured polyester, and a top layer (that is to say, a layer which lies distal to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Therefore, the first transmission layer 326a includes a top surface of the spacer fabric that has more filaments in a yarn used to form it than the number of filaments making up the yarn used to form the bottom spacer fabric layer. The second transmission layer 326b includes a bottom surface of the spacer fabric that has more filaments in a yarn used to form it than the number of filaments making up the yarn used to form the top spacer fabric layer.

This differential between filament counts in the spaced apart layers helps control moisture flow across the transmission layers. Particularly, by having a filament count greater in the surface that contacts the absorbent material, that is to say, the surface that contacts the absorbent material is made from a yarn having more filaments than the yarn used in the surface not in contact with the absorbent layer, liquid tends to be wicked along the surface contacting the absorbent layer more than the layer not in contact with the absorbent layer. In use, this differential tends to draw liquid away from the wound bed and into a central region of the dressing where the absorbent layer 321 helps lock the liquid away.

In other embodiments, the 3D fabric of the second transmission layer can be positioned with the same configuration as the 3D fabric of the first transmission layer. For example, the second transmission layer can also have its top surface of the spacer fabric that has more filaments in a yarn used to form it than the number of filaments making up the yarn used to form the bottom spacer fabric layer.

In some embodiments, the 3D fabric can include different pore sizes on the top and bottom surfaces of the 3D fabric. In some embodiments, the transmission layer can be positioned to place the 3D fabric on either side of the absorbent material with the side of the 3D fabric including the larger pore size facing or in contact with the absorbent layer. The pore size of the 3D fabric and the location of the pores with respect to the other layers of the dressing can be optimized to control fluid handling within the dressing.

Figure 3B:
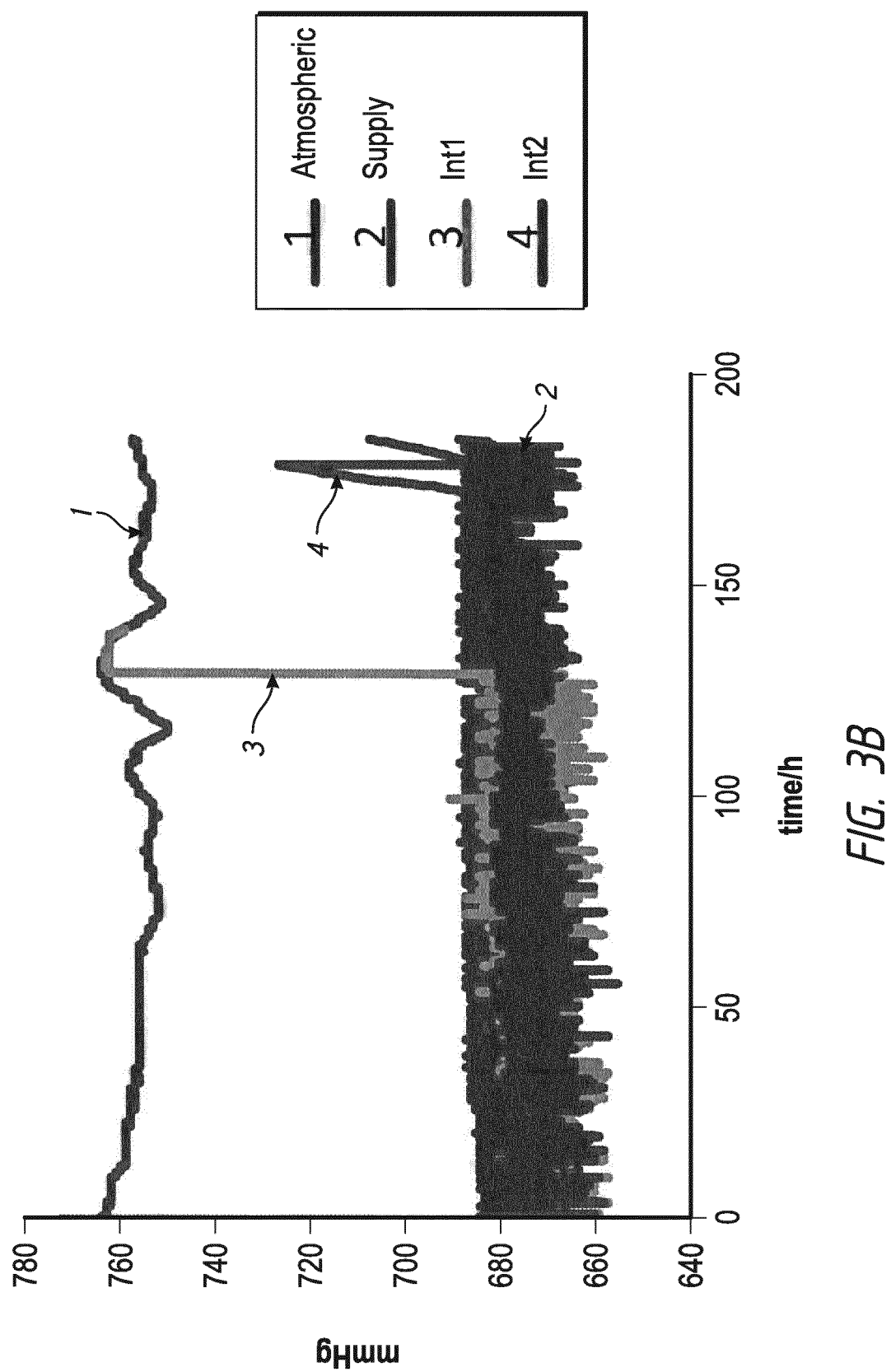
FIG. 3B illustrates the results of a wound model for an embodiment of a negative pressure wound treatment system displaying the onset of vacuum failure.

As shown in the results displayed in FIG. 3B, the onset of vacuum failure on the wound model similar to that described with reference to FIG. 3A did not occur within five days for two replicate tests.

In some embodiments, free liquid could be observed in the second transmission layer 326b after 3 days. This could be similar to the results seen with the earlier-described dressings. The free liquid in the second transmission layer could be due to insufficient absorbent capacity (2) described previously.

Figure 3C:
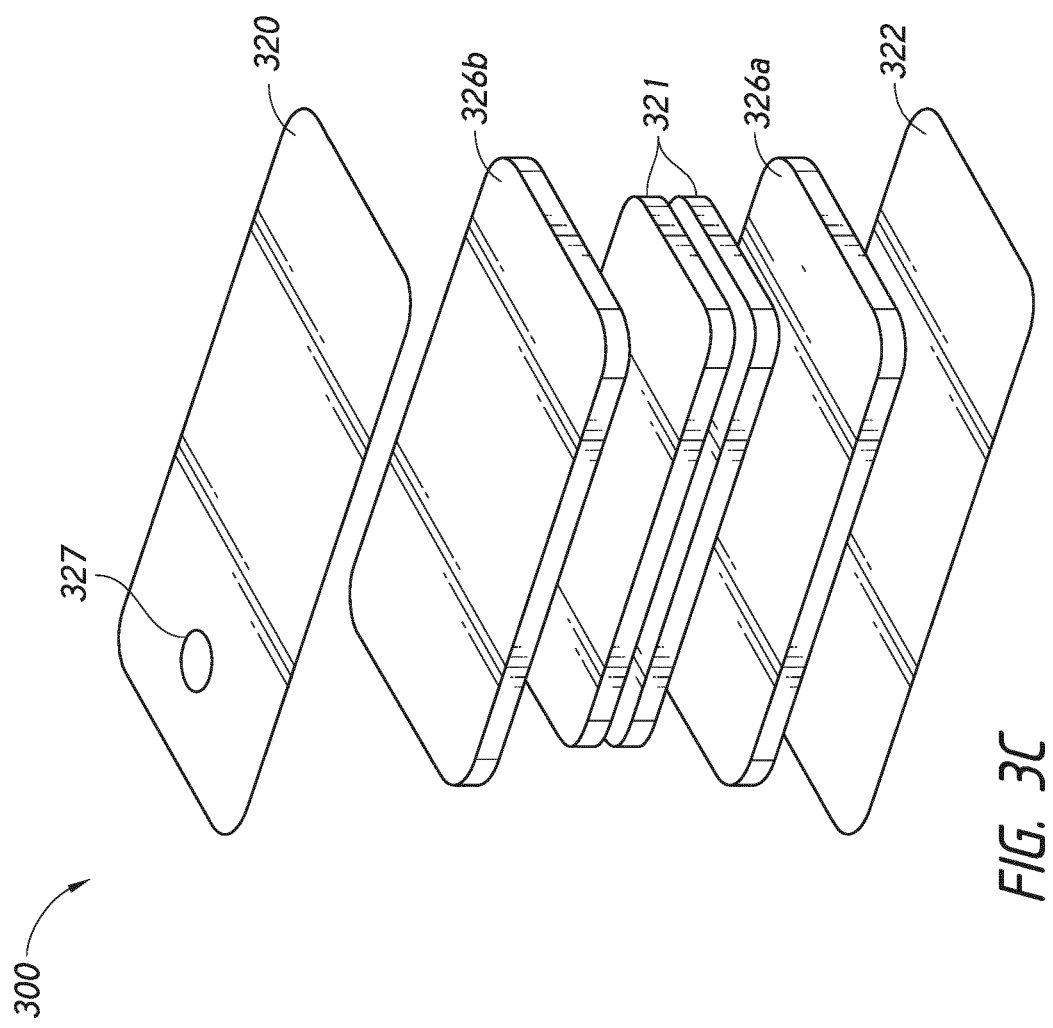
FIG. 3C illustrates an embodiment of a negative pressure wound treatment system employing a wound dressing capable of absorbing and storing wound exudate.

To address this issue, in some embodiments, a further layer of absorbent material can be used between the first and second transmission layers as shown in FIG. 3C. FIG. 3C illustrates a wound dressing with multiple layers similar to the dressing described with reference to FIG. 3A. FIG. 3C also includes a second absorbent layer. The wound dressing can include multiple absorbent layers provided between the first and second transmission layers 326a, 326b.

In some embodiments, as illustrated in FIG. 3D, the second transmission layer can be a cross-shaped transmission layer as opposed to the rectangular shaped transmission layer shown in FIGS. 3A and 3C. The cross-shaped transmission layer 326c can over-border the absorbent layer 321 so that it makes contact with the edges of the first transmission layer 326a positioned below the one or more absorbent layers 321. The cross-shaped transmission layer 326c helps minimize thickness to specific areas of the dressing. This reduction in thickness can assist in maintaining the conformability of the dressing.

Figure 4A:
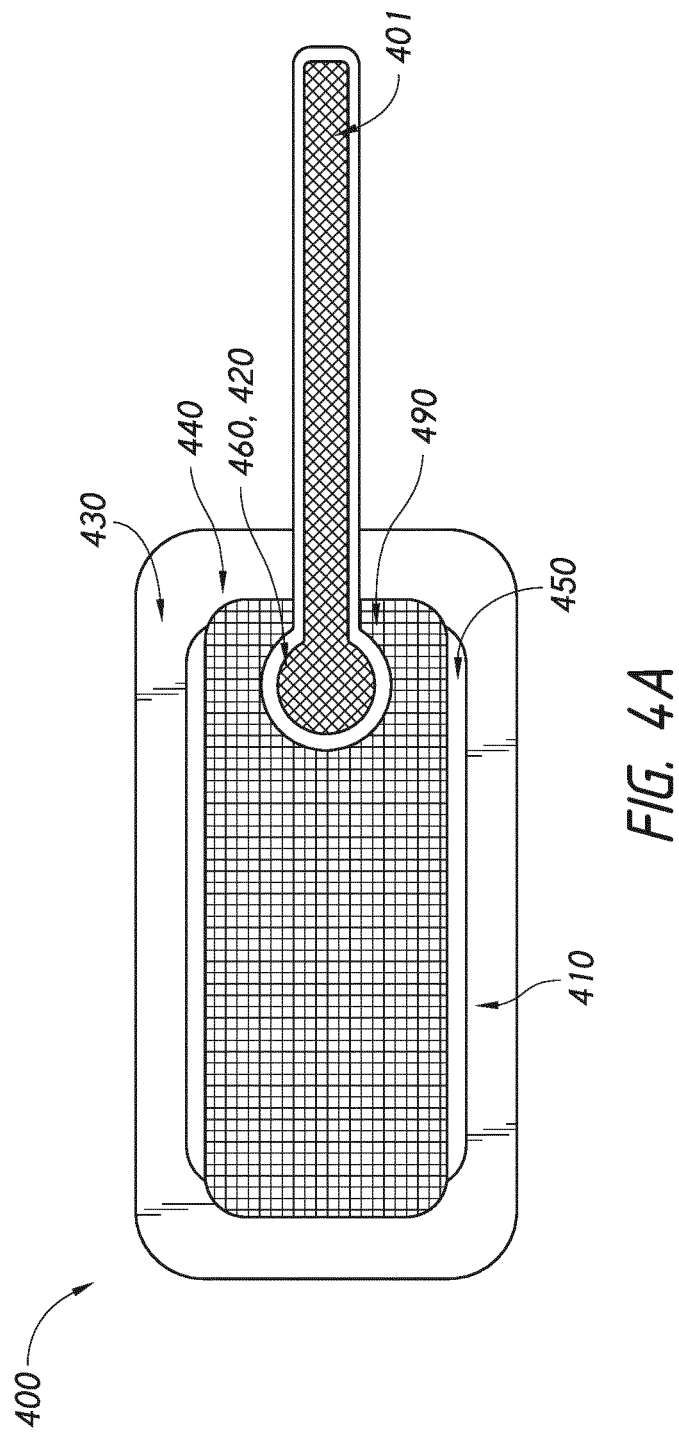
FIG. 4A illustrates an embodiment of a negative pressure wound treatment system employing a flexible fluidic connector and a wound dressing with a wrapped around spacer layer, the wound dressing capable of absorbing and storing wound exudate.

FIG. 4A illustrates an embodiment of a TNP wound treatment device comprising a wound dressing. As stated above, the wound dressing 400 can be any wound dressing embodiment disclosed herein or have any combination of features of any number of wound dressing embodiments disclosed herein. For example, the wound dressing 400 may be similar to a PICO single unit dressing available from Smith & Nephew as described previously. The wound dressing 400 and associated system may also be similar to the system described in FIGS. 1A-1B and 2A-2B previously.

The dressing 400 may be placed over a wound, and a port 460 (which together with conduit 401 may form a fluidic connector as described with respect to FIGS. 1A-1B and 2A-2B) may be used to provide negative pressure from a vacuum source to the wound. In the embodiment shown in FIG. 1A the dressing 400 may be provided with at least a portion of the conduit 401 pre-attached to the port 460. For example, the port/conduit combination may be a flexible suction adapter as described herein with reference to FIGS. 1A-1B and 2A-2B. In some embodiments, the pre-attached conduit 401 can connect to a conduit extension, for example, a tubing (not shown). Preferably, the dressing 400 is provided as a single article with all wound dressing elements (including the port 460 and conduit 401) pre-attached and integrated into a single unit. The wound dressing 400 may then be connected, via the conduit 401 and/or conduit extension, to a source of negative pressure such as the pump as described with reference to FIGS. 1A-1B and 2A-2B.

The cover layer 430, which can be more clearly seen in FIG. 4C, can be formed of substantially fluid impermeable material, such as film. The film may be transparent, such that from the top view of FIG. 4A, other layers underneath the cover layer are also visible. The cover layer can include an adhesive for securing the dressing to the surrounding skin or a wound contact layer. The dressing can utilize a wound contact layer 440 and an absorbent layer 450 within the dressing. The wound contact layer can be configured to be in contact with the wound. The wound contact layer can include an adhesive on the patient facing side for securing the dressing to the surround skin or on the top side for securing the wound contact layer 440 to a cover layer 430 or other layer of the dressing. In operation, in some embodiments the wound contact layer can be configured to provide unidirectional flow so as to facilitate removal of exudate from the wound while blocking or substantially preventing exudate from returning to the wound. Further, an absorbent layer (such as layer 450) for absorbing and retaining exudate aspirated from the wound can be utilized. In some embodiments, the absorbent layer can include an absorbent material, for example, a superabsorbent material or other absorbent material known in the art. In some embodiments, the absorbent layer can include a shaped form of a superabsorber layer with recesses or compartments for the pump, electronics, and accompanying components. In some embodiments, the wound dressing can include multiple absorbent layers.

The absorbent material as shown in FIG. 4A which may be a foam or non-woven natural or synthetic material and which may optionally include or be super-absorbent material, forms a reservoir for fluid, particularly liquid, removed from the wound site and draws those fluids towards a cover layer 430. The material of the absorbent layer can be similar to the absorbent material described with reference to FIG. 2B. The material of the absorbent layer also prevents liquid collected in the wound dressing from flowing in a sloshing manner. The absorbent layer 450 also helps distribute fluid throughout the layer via a wicking action so that fluid is drawn from the wound site and stored throughout the absorbent layer. This helps prevent agglomeration in areas of the absorbent layer.

In some embodiments, the absorbent layer is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing.

The wicking action also assists in delivering liquid downwards towards the wound bed when exudation slows or halts. This delivery process helps maintain the transmission layer or lower spacer layer and lower wound bed region in a moist state which helps prevent crusting within the dressing (which could lead to blockage) and helps maintain an environment optimized for wound healing.

In some embodiments, the absorbent layer may be an air-laid material. Heat fusible fibers may optionally be used to assist in holding the structure of the pad together. It will be appreciated that rather than using super-absorbing particles or in addition to such use, super-absorbing fibers may be utilized according to certain embodiments of the present invention. An example of a suitable material is the Product Chem-Posite™ 11 C available from Emerging Technologies Inc (ETi) in the USA.

Optionally, according to certain embodiments of the present invention, the absorbent layer may include synthetic stable fibers and/or bi-component stable fibers and/or natural stable fibers and/or super-absorbent fibers. Fibers in the absorbent layer may be secured together by latex bonding or thermal bonding or hydrogen bonding or a combination of any bonding technique or other securing mechanism. In some embodiments, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer may comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer comprises a pad of cellulose fibers and a plurality of super absorbent particles. In additional embodiments, the absorbent layer is a non-woven layer of randomly orientated cellulose fibers.

Super-absorber particles/fibers may be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc.

Preferably, the particles of superabsorber are very hydrophilic and grab the fluid as it enters the dressing, swelling up on contact. An equilibrium is set up within the dressing core whereby moisture passes from the superabsorber into the dryer surrounding area and as it hits the top film the film switches and the fluid vapor starts to be transpired. A moisture gradient is established within the dressing to continually remove fluid from the wound bed and ensure the dressing does not become heavy with exudate.

The absorbent layer can include at least one through hole. The through hole can be located so as to underlie the suction port as described with reference to FIG. 2B. A single through hole can be used to produce an opening underlying the port 460 (not shown in FIG. 4C, but shown as opening 511 in FIG. 4D). It will be appreciated that multiple openings could alternatively be utilized. Additionally, should more than one port be utilized according to certain embodiments of the present invention one or multiple openings may be made in the super-absorbent layer in registration with each respective port. Although not essential to certain embodiments of the present invention the use of through holes in the super-absorbent layer provide a fluid flow pathway which is particularly unhindered and this is useful in certain circumstances.

Use of one or more through holes in the absorption layer also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the lower spacer layer and the upper spacer layer to the wound facing surface of the filter and then onwards into the interior of the port.

These layers can be covered with one layer of a film or cover layer. The cover layer can include a filter that can be positioned over the absorbent layer, or a filter may be incorporated in the port 460 as described in International Application Publication No. WO 2013/175306 A2, U.S. Publication No. US2011/0282309, and U.S. Publication No. 2016/0339158 the entirety of which is hereby incorporated by reference. As shown in FIG. 4A gas impermeable, but moisture vapor permeable, cover layer 430 extends across the width of the wound dressing. The cover layer may be similar to the cover layer or backing layer described with reference to FIG. 2B. The cover layer, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 430 is sealed to the wound contact layer 440 in a border region 410 around the circumference of the dressing, ensuring that no air is drawn in through the border area, for example via adhesive or welding techniques. The cover layer 430 protects the wound from external bacterial contamination (bacterial barrier) and allows liquid from wound exudates to be transferred through the layer and evaporated from the film outer surface. The cover layer 430 typically comprises two layers; a polyurethane film and an adhesive pattern spread onto the film. The polyurethane film is moisture vapor permeable and may be manufactured from a material that has an increased water transmission rate when wet.

The cover layer can include an aperture within the cover layer for providing fluid communication with a source of negative pressure or pump. The filter can be positioned in communication with the aperture in the wound cover. The aperture in the wound cover can be covered by a port 460. In some embodiments, the port 460 connects to a conduit for communication with a negative pressure source or pump. The port 460 can include a filter 420 provided to cover the aperture in the cover layer 430. In some embodiments, the filter 420 can be integral to the port 460. The filter 420 can include hydrophobic material to protect the pump and/or other components from liquid exudates. The filter 420 can block fluids while permitting gases to pass through. In some embodiments, the aperture in the cover layer 430 and the port 460 provide fluid communication between the wound dressing and a pump. In some embodiments, the pump, electronics, switch and battery can be positioned at a remote location from the dressing. In some embodiments, the pump, electronics, switch and battery can be positioned on top of the first cover layer and a second filter and second cover layer can be alternative or additionally used. For example, the second filter can be constructed from antibacterial and/or antimicrobial materials so that the pump can exhaust gases into the atmosphere. The second filter can also help to reduce noise produced by the pump.

Negative pressure can be lost at the wound bed when free absorbent capacity remains in the dressing. This can occur because some or all of the pores in the filter are blocked with liquid or particulates. In some embodiments, solutions are utilized to allow the full capacity of the dressing absorbent layer to be utilized whilst maintaining the air path between the source of negative pressure and the wound bed.

In dressing embodiments that utilize a cover layer directly over the absorbent layer the dressing can have a void underneath the filter which can fill with liquid, thus blocking the filter pores and preventing air flow to the wound bed. A spacer layer 490 can be used to provide a fluid flow path above the absorbent layer 450 preventing the blocking of the port 460. In some embodiments, the spacer layer 490 in the dressing can be provided above and below the absorbent layer. The spacer layer can be incompressible and maintain a path for fluid flow between the source of negative pressure and the wound bed, via the filter. In some embodiments, the spacer layer can encapsulate or wrap around the absorbent layer as shown in FIG. 4A. The wrapped spacer layer can provide an uninterrupted length of spacer material from the filter 420 to the wound bed. The spacer layer can traverse the length of the top surface of the absorbent layer and wrap around at least one side of the absorbent layer and traverse the length of the bottom surface (wound facing surface) of the absorbent layer. In some embodiments, the spacer layer can wrap around two sides of the absorbent layer as shown in FIG. 4A.

In some embodiments, the spacer layer can be utilized to assist in distributing negative pressure over the wound site and facilitating transport of wound exudate and fluids into the wound dressing.

A lower portion spacer layer 490 of porous material can be located above the wound contact layer and below the absorbent layer and wrapped around the edges of the absorbent layer. As the spacer layer is wrapped around at least one edge of the absorbent layer, the spacer layer has an upper portion of the spacer layer that can be positioned between the cover layer and the absorbent layer. As used herein the edge of the absorbent layer or the dressing refers to the sides of the material that are substantially perpendicular to the wound surface and run along the height of the material.

In some embodiments, the spacer layer can be a porous layer. This spacer layer, or transmission layer, 490 allows transmission of fluid including liquid and gas away from a wound site into upper layers of the wound dressing as described with reference to FIG. 2B. In particular, the spacer layer 490 ensures that an open air channel can be maintained to communicate negative pressure over the wound area even when the absorbent layer has absorbed substantial amounts of exudates. The layer should remain open under the typical pressures that will be applied during negative pressure wound therapy as described previously, so that the whole wound site sees an equalized negative pressure. The spacer layer 490 may be formed of a material having a three dimensional structure. For example, a knitted or woven spacer fabric (for example Baltex 7970 weft knitted polyester) or a non-woven fabric could be used. Other materials, such as those described previously herein, could of course be utilized.

In some embodiments, the spacer layer comprises a 3D polyester spacer fabric layer including a first layer which is a 84/144 textured polyester, and a second layer which is a 100 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The first spacer fabric thus has more filaments in a yarn used to form it than the number of filaments making up the yarn used to form the second spacer fabric layer. This differential between filament counts in the spaced apart layers helps control moisture flow across the spacer layer. Particularly, by having a filament count greater in the first layer, that is to say, the first layer is made from a yarn having more filaments than the yarn used in the second layer, liquid tends to be wicked along the first layer more than the second layer. In use, the first layer can be placed in contact with the absorbent layer and this differential between the first layer and the second layer tends to draw liquid away from the wound bed and into a central region of the dressing where the absorbent layer helps lock the liquid away or itself wicks the liquid onwards towards the cover layer where it can be transpired.

Preferably, to improve the liquid flow across the spacer layer (that is to say perpendicular to the channel region formed between the first and second spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the spacer layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Whilst certain embodiments of the present invention have so far been described in which the spacer layer is formed as a 3D knit layer, e.g., two layers spaced apart by a monofilament layer, it will be appreciated that certain embodiments of the present invention are not restricted to the use of such a material. In some embodiments, as an alternative to such a 3D knit material one or more layers of a wide variety of materials could be utilized. In each case, according to embodiments of the present invention, the openings presented by layers of the spacer layer are wider and wider as one moves away from the side of the dressing which, in use will be located proximate to the wound. In some embodiments, the spacer layer may be provided by multiple layers of open celled foam. In some embodiments, the foam is reticulated open cell foam. Preferably, the foam is hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In certain embodiments, two, three, four or more foam layers may be included. The foam layers may be integrally formed, for example, by selecting a foam having a large pore size and then repeatedly dipping this to a lesser and lesser extent into material which will clog the pores or alternatively, the spacer layer formed by the multiple foam layers may be provided by laminating different types of foam in a layered arrangement or by securing such layers of foam in place in a known manner.

According to certain embodiments of the present invention, the spacer layer is formed by multiple layers of mesh instead of foam or 3D knit materials. For example, fine gauze mesh may be utilized for a wound facing side of the spacer layer and a Hessian mesh having a larger pore size may be located on a distal side of the gauze mesh facing away from the wound in use. The one, two, three or more layers of mesh can be secured together in an appropriate manner, such as being stitched or adhered together or the like. The resultant mat of fibers provides a transmittal layer through which air can be transmitted in the dressing but by selecting the opening sizes in the meshes as one moves through the dressing away from the wound contact side, the accumulation of solid particulate matter in lower layers can be avoided. The materials described with reference to FIGS. 4A-4E can apply to the materials described for these embodiments or elsewhere in the specification.

FIG. 4A illustrates a top view of an embodiment of a wound dressing with a spacer layer 490 wrapped around an absorbent layer 450. The wound dressing can be constructed with a wound contact layer 440 and a top film or cover layer 430 enclosing an absorbent layer 450. A hole or aperture in the top film 430 can be entirely covered by a port 460 which leads to a source of negative pressure. The port 460 can contain a filter 420 or can be positioned over the filter 420. The dressing absorbent layer 450 can comprise a superabsorbent material. The absorbent layer 450 can be surrounded fully or in part by a spacer fabric or spacer layer 490. The spacer layer 490 can be provided above and below the absorbent layer 450. In some embodiments, the spacer layer 490 can be wrapped around and cover two sides the absorbent layer 450. For example, in some embodiments, a length of the spacer layer 490 can be configured to provide a fluid flow that connects the wound contact surface 440 and the filter 420. As illustrated in FIG. 4A, the spacer layer can extend around the absorbent layer 450 running along the length of the bottom surface and top surface of the absorbent layer and wrapping around at least one side of the absorbent layer but not fully encapsulating the absorbent layer. In some embodiments, as shown in FIG. 4A, the spacer layer 490 extends to the periphery of the absorbent layer but does not extend over the ends of the width of the dressing. For example, as illustrated in FIG. 4A, the periphery of two sides of the absorbent layer 450 extend beyond the spacer layer 490 while the spacer layer extends over and wraps around the other two sides of the absorbent layer. In other embodiments, the spacer layer 490 fully encapsulates and all sides of the absorbent layer 450.

The port 460 can be positioned either above the top film or cover layer 430 at one end or in the center of the dressing. The port can be positioned over the aperture in the top film and can contain or be placed over the filter 420. As described herein, providing the spacer layer above and below and wrapped around at least one side of the absorbent layer can prevent the filter from becoming blocked with liquid or particulates, by allowing the distribution of fluid through the wrapped spacer layer until the full absorbent capacity of the dressing materials have been reached. This can increase the wear time of the wound dressing by prolonging delivery of negative pressure to the wound bed. In some embodiments, the dressing with the configuration of layers as described herein has demonstrated a longer delivery period of NPWT to the wound contact surface compared to wound dressing without the spacer layer between the absorbent layer and the cover layer and without the spacer layer wrapped around the absorbent layer.

Although FIG. 4A illustrates the port 460 situated entirely over the absorbent layer, in some embodiments, the dressing 400 can have the port 460 situated along part or all of one edge of the absorbent layer area. In some embodiments, the dressing 400 can have the port 460 in a band around the edge of the absorbent layer area.

Figure 4B:
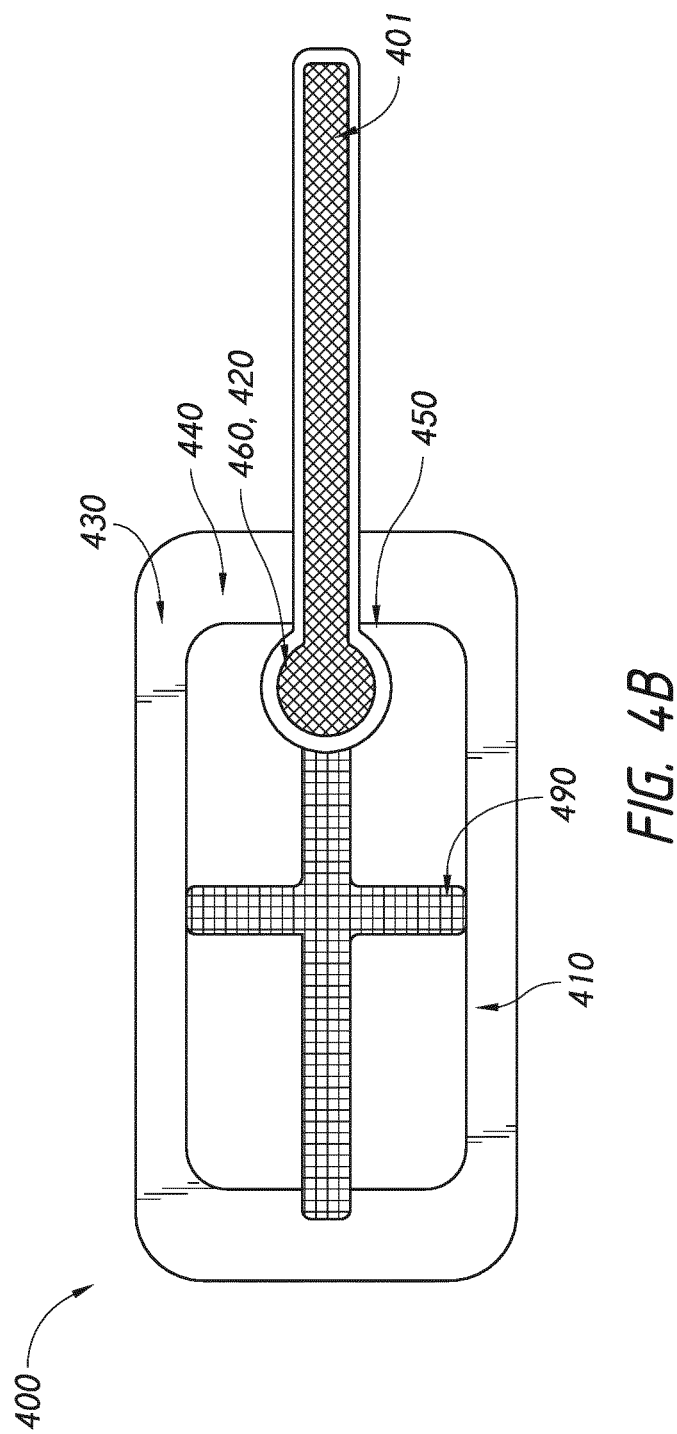
FIG. 4B illustrates an embodiment of a negative pressure wound treatment system employing a flexible fluidic connector and a wound dressing with a wrapped around spacer layer with a cross shaped configuration, the wound dressing capable of absorbing and storing wound exudate.

FIG. 4B illustrates a top view of an embodiment of a wound dressing 400. The wound dressing 400 of FIG. 4B is similar to the wound dressing 400 as described with reference to FIG. 4A except the spacer layer includes a cross shaped spacer layer 490 wrapped around an absorbent layer 450. The wound dressing can have a top film or cover layer 430 as an upper layer of the dressing or the layer furthest from the wound while in use. The wound dressing can include a wound contact layer 440 as the lower layer of the dressing. A port 460 containing a filter can be provided above or within the cover layer 430. The wound dressing can include an absorbent layer 450 and the absorbent layer 450 can include a superabsorber or superabsorbent material. The spacer fabric or spacer layer 490 can comprise a thin strip of spacer fabric that wraps around a length and width of the absorbent layer creating a cross shaped channel for fluid flow around the absorbent layer as shown in FIG. 4B. In other embodiments, the spacer layer 490 includes a bottom portion along the bottom surface of the absorbent layer that is rectangular shaped and thin strips of the spacer fabric extend from the rectangular bottom portion to wrap around the absorbent layer 450 forming the cross shaped spacer layer as shown in FIG. 4B above the absorbent layer 450. In some embodiments, the cross shaped spacer layer includes a cross shaped spacer layer below the absorbent layer 450 that wraps around the end of the absorbent layer to form the cross shaped layer above the absorbent layer. In some embodiments, the cross shaped spacer layer is formed from one piece of spacer fabric that is folded around the absorbent. In other embodiments, the cross shaped spacer layer is formed of two pieces of spacer fabric that cross each other in the middle and are wrapped around the end of the absorbent. In some embodiments, the cross shaped layer is formed from four pieces of spacer fabric.

FIG. 4C illustrates a cross-sectional view of the wound dressing with the spacer layer 490 wrapped around the absorbent layer 450. As shown in FIG. 4C, the wound contact layer 440 can be provided as the bottom layer of the dressing configured to contact the wound surface. The top film or cover layer 430 is provided as a top layer enclosing the spacer layer 490 and the absorbent layer 450 with the wound contact layer 440. The cover layer 430 can seal to the border region around the periphery of the wound contact layer 440, the skin of a patient, and/or the wound bed. The port 460 can be positioned above the cover layer 430 and over an aperture in the cover layer 430. As illustrated in FIG. 4C, the cross section of the wound dressing shows the spacer layer 490 surrounding the absorbent layer 450 so that the port 460 is in communication with the upper portion of spacer material and the wound contact layer is in contact with the lower portion of the spacer material. The configuration of the spacer layer surrounding the absorbent material allows a fluid flow path from the wound bed or wound contact layer to the port without passing through the absorbent layer.

The spacer layer 490 can be wrapped around the absorbent layer 450 to disperse the vacuum throughout the dressing. In some embodiments, the spacer layer 490 can be manufactured as one flat piece of material that during assembly of the dressing is positioned on the bottom surface of the absorbent layer 450, wrapped around the ends of the absorbent layer 450, and the two ends of the spacer layer 490 are folded over the top surface of the absorbent layer 450 completely or partially covering the top surface of the absorbent layer 450. In such embodiments, the upper spacer layer 490 can have a break 495 in the spacer material where the two folded over ends of the spacer material 490 meet as shown in FIG. 4C. In alternative embodiments, the spacer layer 490 can be manufactured as one piece of spacer material that is pre-shaped to fit around the absorbent layer 450 and fully encapsulates the absorbent layer 450 with no break in the spacer material as shown in FIG. 4D.

Providing the spacer layer between the port and the absorbent layer prevents fluid or exudate removed from the wound from blocking the port and/or filter within the port. There can be some free particles in the hole of the absorbent layer positioned below the filter. The loose free particles in the hole can gel and block the hole and/or filter area. Therefore, the upper spacer layer can keep the superabsorber particles clear from the filter and allow the dressing to fill completely. In some embodiments, the spacer layer wrapped around the absorbent layer allow the port to be located at any location with respect to gravity. The spacer layer positioned above the absorbent layer can eliminate the concerns of the fluid or exudate removed from the wound from blocking the port and/or filter within the port on the section of the absorbent layer that is filled first.

FIG. 4D illustrates a cross-section of an integrated wound dressing 500 showing the various layers according to some embodiments. The embodiment of FIG. 4D shows a cross section of the wound dressing similar to the cross section shown in FIGS. 4A-4C. The dressing can include spacer layer portions above 592 and below 591 the absorbent layer 550 and wrapped around at least two sides of the absorbent layer 550. The bottom or lower portion 591 of the spacer layer is positioned between the wound contact layer 540 and the absorbent layer 550. The upper portion 592 of the spacer layer is positioned between the cover layer 530 and the absorbent layer 550. In some embodiments, the dressing can include a hole 511 in an absorbent layer 550. The dressing includes a cover layer 530 and a wound contact layer 540 and the absorbent layer 550 can be wrapped in the spacer layer 590 enclosed in the cover layer 530 and the wound contact layer 540. The hole 511 in the absorbent layer can be positioned below the port 560. In some embodiments, the hole 511 in the absorbent layer can provide a fluid flow path from the lower portion 591 of the spacer layer 590 and the upper portion 592 of the spacer layer 590 without traversing the absorbent layer 550.

Figure 4E:
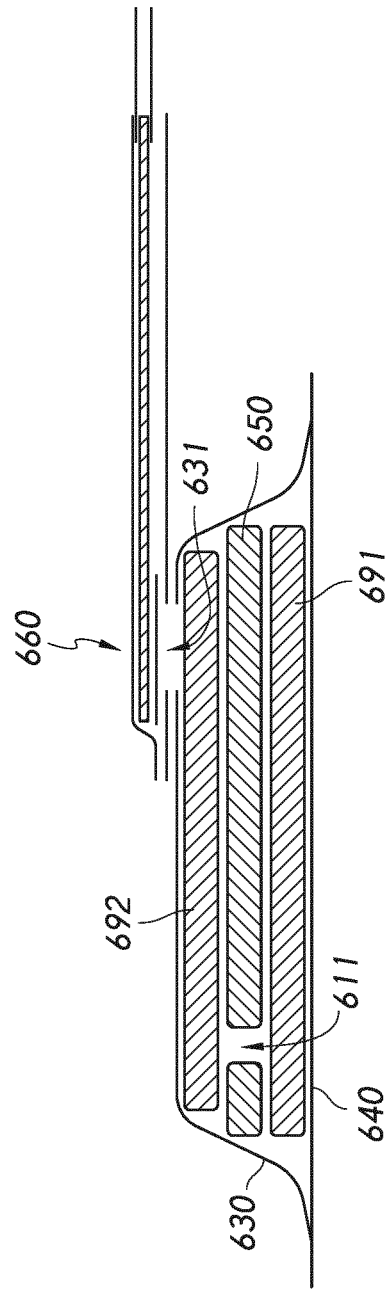
FIG. 4E illustrates a cross-section of an integrated wound dressing showing various layers according to another embodiment.

FIG. 4E illustrates a cross-section of an integrated wound dressing 600. The dressing comprises the various layers as described with reference to FIGS. 4A-D. The dressing can include a spacer layer portion above 692 and a spacer layer portion below 691 the absorbent layer 650. The cross sectional view of the dressing shown in FIG. 4E illustrates a view where the wrapped edges of the spacer layer and absorbent layer are not visible. In other embodiments, the portions 692 and 691 may be discrete layers that do not wrap around the absorbent layer. The bottom or lower portion 691 of the spacer layer is positioned between the wound contact layer 640 and the absorbent layer 650. The upper portion 692 of the spacer layer is positioned between the cover layer 630 and the absorbent layer 650. In some embodiments, the dressing can include a hole 611 in an absorbent layer 650. The hole 611 in the absorbent layer 650 can be off set from the port 660 over the aperture 631 in the cover layer 630 and the wrapped spacer layer can bridge the gap for the communication between the hole 611 and the port 660.

In some embodiments, the hole in absorbent layer can be optional as the fluid communication can be bridged around the absorbent layer by the wrapped spacer layer. Additionally, in some embodiments, the dressing can have a port offset from the hole in the absorbent layer to allow fluid to drop back down into the absorbent layer as the fluid passes through the wrapped spacer layer toward the port in communication with a negative pressure source. In some embodiments, the wrapped spacer layer can cover any exposed fibers from the absorbent material that makes up the absorbent layer. The exposed fibers can potentially pierce the top film or cover layer and the wrapped spacer layer can eliminate the exposed fibers from coming into contact with the cover layer and piercing the cover layer.

In some embodiments, the dressing with a spacer fabric or spacer layer cast around a central layer of absorbent material. In some embodiments, a fluid channel can be maintained throughout the spacer material and between the filter and wound contact surface. In other embodiments, the dressing can have an absorbent layer or superabsorbent material cast around a central layer of spacer fabric. A fluid channel can be maintained throughout the absorbent material and between the filter and wound contact surface.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, and/or adjacent to the backing layer. In some embodiments, the wound dressing can include a second cover layer and/or a second filter layer for positioning over the layers of the wound dressing and any of the integrated components. The second cover layer can be the upper most layer of the dressing or can be a separate envelope that enclosed the integrated components of the topical negative pressure system.

Figure 5A:
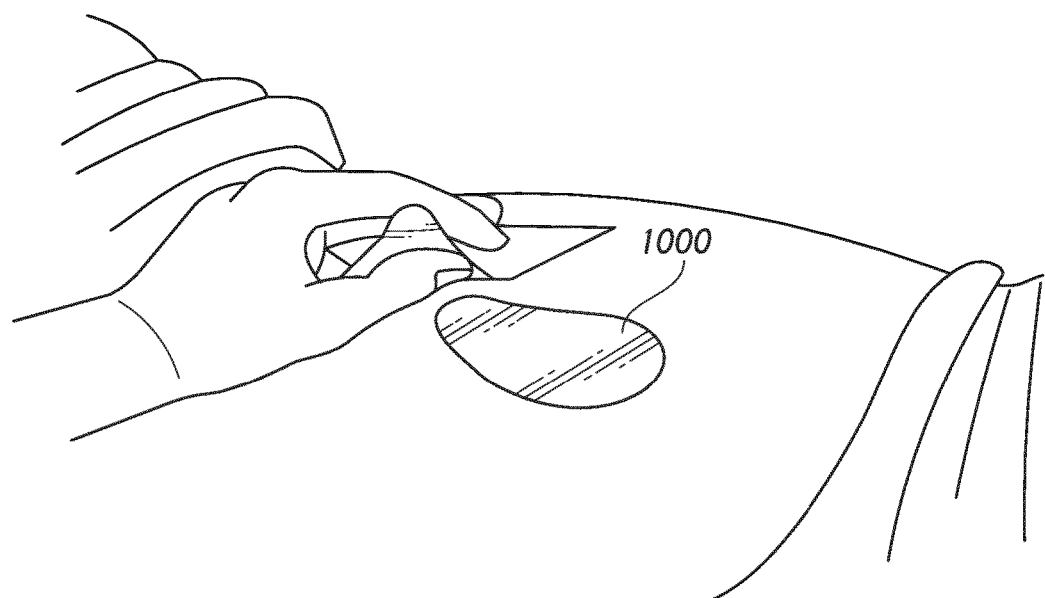
FIGS. 5A-D illustrate the use and application of an embodiment of a wound treatment system onto a patient.

FIGS. 5A-D illustrate the use of an embodiment of a negative pressure therapy wound treatment system being used to treat a wound site on a patient. FIG. 5A shows a wound site 1000 being cleaned and prepared for treatment. Here, the healthy skin surrounding the wound site 1000 is preferably cleaned and excess hair removed or shaved. The wound site 1000 may also be irrigated with sterile saline solution if necessary. Optionally, a skin protectant may be applied to the skin surrounding the wound site 1000. If necessary, a wound packing material, such as foam or gauze, may be placed in the wound site 1000. This may be preferable if the wound site 1000 is a deeper wound.

Figure 5B:
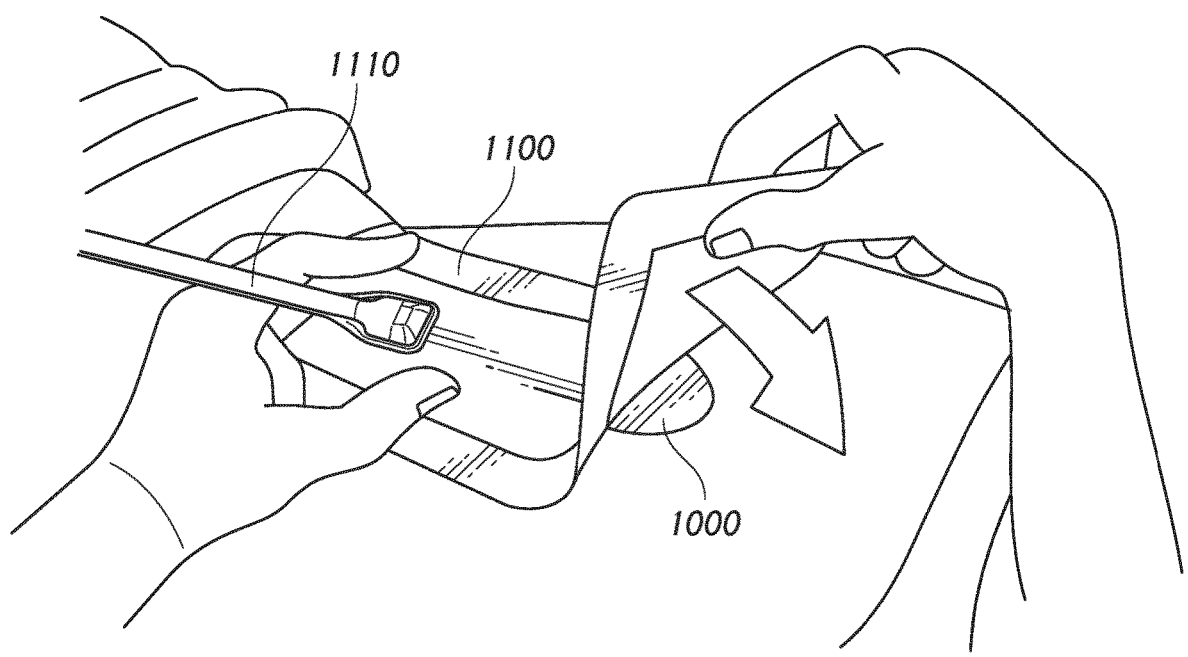

After the skin surrounding the wound site 1000 is dry, and with reference now to FIG. 5B, the wound dressing 1100 may be positioned and placed over the wound site 1000. Preferably, the wound dressing 1100 is placed with the wound contact layer over and/or in contact with the wound site 1000. In some embodiments, an adhesive layer is provided on the lower surface of the wound contact layer, which may in some cases be protected by an optional release layer to be removed prior to placement of the wound dressing 1100 over the wound site 1000. Preferably, the dressing 1100 is positioned such that the fluidic connector 1110 is in a raised position with respect to the remainder of the dressing 1100 so as to avoid fluid pooling around the port. In some embodiments, the dressing 1100 is positioned so that the fluidic connector 1110 is not directly overlying the wound, and is level with or at a higher point than the wound. To help ensure adequate sealing for TNP, the edges of the dressing 1100 are preferably smoothed over to avoid creases or folds.

Figure 5C:
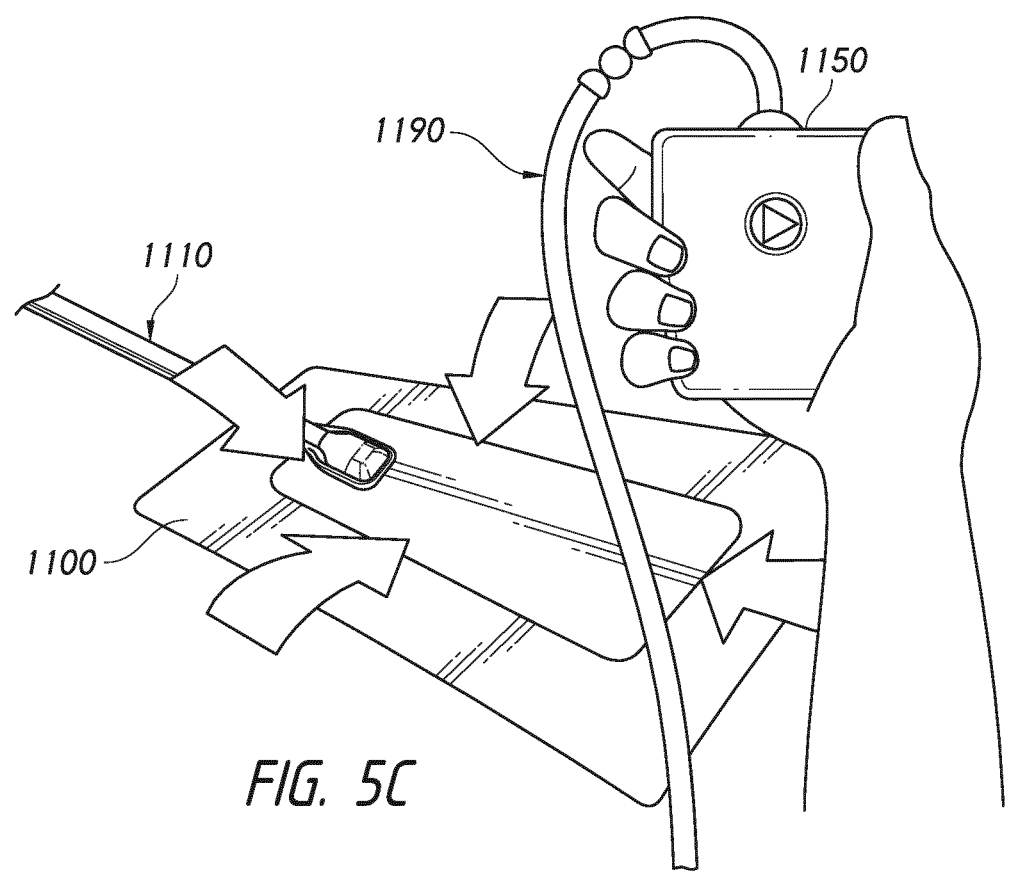

With reference now to FIG. 5C, the dressing 1100 is connected to the pump 1150. The pump 1150 is configured to apply negative pressure to the wound site via the dressing 1100, and typically through a conduit. In some embodiments, and as described herein, a fluidic connector 1110 may be used to join the conduit 1190 from the pump to the dressing 1100. Where the fluidic connector is adhered to the top layer of the wound dressing, a length of tubing may be coupled at a first end of the fluidic connector such that the tubing, or conduit, extends away from the fluidic connector parallel to the top of the dressing. In some embodiments, the conduit may comprise a fluidic connector. It is expressly contemplated that a conduit may be a soft bridge, a hard tube, or any other apparatus which may serve to transport fluid. Upon the application of negative pressure with the pump 1150, the dressing 1100 may in some embodiments partially collapse and present a wrinkled appearance as a result of the evacuation of some or all of the air underneath the dressing 1100. In some embodiments, the pump 1150 may be configured to detect if any leaks are present in the dressing 1100, such as at the interface between the dressing 1100 and the skin surrounding the wound site 1000. Should a leak be found, such leak is preferably remedied prior to continuing treatment.

Figure 5D:
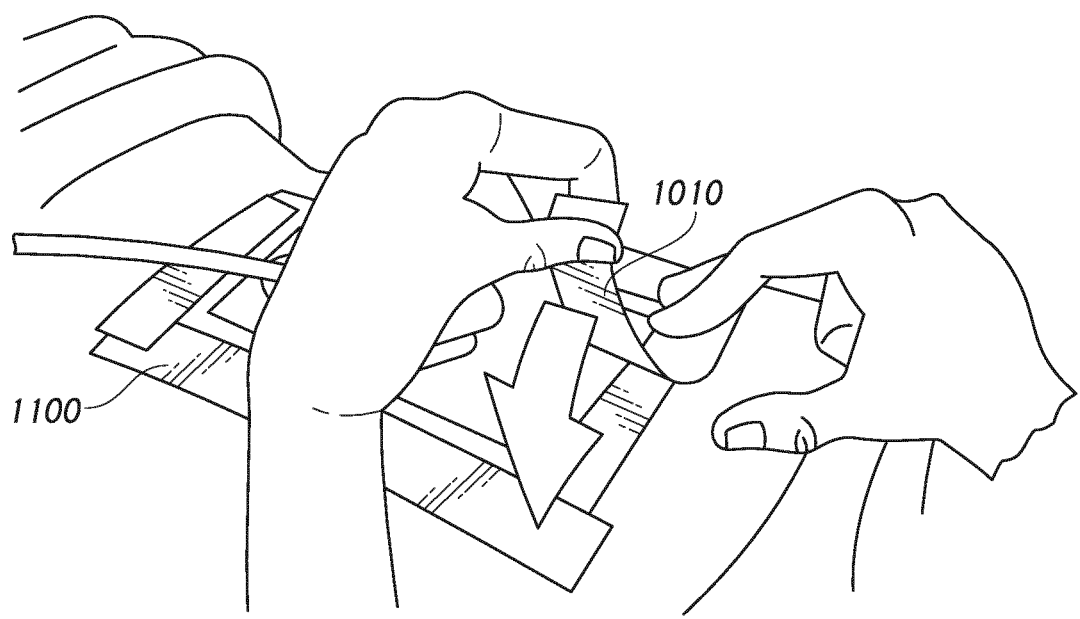

Turning to FIG. 5D, additional fixation strips 1010 may also be attached around the edges of the dressing 1100. Such fixation strips 1010 may be advantageous in some situations so as to provide additional sealing against the skin of the patient surrounding the wound site 1000. For example, the fixation strips 1010 may provide additional sealing for when a patient is more mobile. In some cases, the fixation strips 1010 may be used prior to activation of the pump 1150, particularly if the dressing 1100 is placed over a difficult to reach or contoured area.

Treatment of the wound site 1000 preferably continues until the wound has reached a desired level of healing. In some embodiments, it may be desirable to replace the dressing 1100 after a certain time period has elapsed, or if the dressing is full of wound fluids. During such changes, the pump 1150 may be kept, with just the dressing 1100 being changed.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A negative pressure wound therapy apparatus, comprising:
   a wound dressing comprising:
      a wound contact layer configured to be positioned in contact with a wound;
      an absorbent layer;
      a spacer layer above the absorbent layer, the spacer layer having an edge that extends beyond a perimeter of the absorbent layer, wherein the spacer layer only partially covers the absorbent layer, wherein the edge of the spacer layer is configured to provide a fluid pathway around a portion of the absorbent layer; and a cover layer comprising a moisture vapor permeable material, the cover layer configured to cover and form a seal over the wound contact layer, the spacer layer, and the absorbent layer, and wherein a portion of the absorbent layer is in contact with the cover layer and configured to bring liquid into contact with the cover layer to aid in transpiration of moisture vapor through the cover layer.

2. The wound therapy apparatus of claim 1, further comprising an aperture in the cover layer and a fluidic connector positioned over the aperture in the cover layer.

3. The wound therapy apparatus of claim 2, further comprising a filter provided at the aperture in the cover layer.

4. The wound therapy apparatus of claim 2, wherein the spacer layer underlies the aperture in the cover layer.

5. The wound therapy apparatus of claim 2, further comprising a negative pressure source configured to apply negative pressure through the aperture in the cover layer.

6. The wound therapy apparatus of claim 1, wherein the spacer layer forms a cross-shape above the absorbent layer.

7. The wound therapy apparatus of claim 3, further comprising a through-hole extending through the absorbent layer.

8. The wound therapy apparatus of claim 7, wherein the through-hole is aligned underneath the filter.

9. The wound therapy apparatus of claim 7, wherein the through-hole is offset from the filter.

10. The wound therapy apparatus of claim 1, wherein the spacer layer extends laterally along an upper surface of the absorbent layer.

11. The wound therapy apparatus of claim 1, wherein the spacer layer extends in one or more lateral directions along an upper surface of the absorbent layer.

12. The wound therapy apparatus of claim 1, wherein the spacer layer comprises a strip extending along an upper surface of the absorbent layer.

13. The wound therapy apparatus of claim 12, wherein the strip wraps around the perimeter of the absorbent layer and extends along a lower surface of the absorbent layer.

* * * * *